United States Patent
Fontana et al.

(10) Patent No.: US 12,207,974 B2
(45) Date of Patent: Jan. 28, 2025

(54) MULTI-USER SYSTEM FOR THE ACQUISITION, GENERATION AND PROCESSING OF ULTRASOUND IMAGES

(71) Applicant: Esaote S.p.A., Genoa (IT)

(72) Inventors: Franco Fontana, Genoa (IT); Marco Crocco, Ovada (IT); Paolo Pellegretti, Genoa (IT)

(73) Assignee: Esaote S.p.A., Genoa (IT)

( * ) Notice: Subject to any disclaimer, the term of this patent is extended or adjusted under 35 U.S.C. 154(b) by 372 days.

(21) Appl. No.: 17/740,030

(22) Filed: May 9, 2022

(65) Prior Publication Data
US 2022/0361849 A1    Nov. 17, 2022

(30) Foreign Application Priority Data
May 13, 2021   (IT) .................. 102021000012335

(51) Int. Cl.
*A61B 8/08*   (2006.01)
*G06T 7/00*   (2017.01)

(52) U.S. Cl.
CPC .......... *A61B 8/5207* (2013.01); *A61B 8/5223* (2013.01); *G06T 7/0012* (2013.01)

(58) Field of Classification Search
CPC ....... A61B 8/5207; A61B 8/5223; A61B 8/08; G06T 7/0012; G06T 7/00
See application file for complete search history.

(56) References Cited

U.S. PATENT DOCUMENTS

| | | |
|---|---|---|
| 2005/0265267 A1 | 12/2005 | Hwang |
| 2015/0313578 A1* | 11/2015 | Yu ................... A61B 8/4254 600/459 |
| 2017/0105701 A1 | 4/2017 | Pelissier et al. |

OTHER PUBLICATIONS

Italian Search Report and Written Opinion dated Jan. 26, 2022, which issued in the corresponding Italian Patent Application No. IT 202100012335.

* cited by examiner

*Primary Examiner* — Tuan H Nguyen
(74) *Attorney, Agent, or Firm* — Dickinson Wright PLLC

(57) ABSTRACT

A multi-user system for acquiring, generating and processing ultrasound images comprises: a plurality of ultrasound probes with a communication unit for transmitting corresponding data to one or more processing units also with a communication unit; display and/or user interface terminals with a communication unit for transmitting to and receiving data from said processing units and/or said probes; a communication network connecting together the communication units of said probes, display and/or user interface terminals and said processing units. Processing units are configured to receive scanning signals detected by said probes and process said signals to generate ultrasound images and optionally process said ultrasound images and to transmit said images and/or outputs of said processing to said display and/or user interface terminals. Probes and/or processing units are loaded programs with encoded instructions to receive data from each of said probes and to generate the corresponding images and/or to perform the corresponding processing.

12 Claims, 7 Drawing Sheets

| Probe | LOCAL PROCESSING UNIT | CENTRAL PROCESSING UNIT | MONITOR AND USER INTERFACE |
|---|---|---|---|
| Transmission and reception | D/A conversion in TX and A/D conversion in RX | Beamforming in TX e in RX<br>Image Forming<br>Back-end processing<br>Further processing | Display<br>Command input |
| Transmission and reception | D/A conversion in TX and A/D conversion in RX<br>Beamforming in TX e in RX | Image Forming<br>Back-end processing<br>Further processing | Display<br>Command input |
| Transmission and reception | D/A conversion in TX and A/D conversion in RX<br>Beamforming in TX and in RX<br><br>Image Forming<br>Back-end processing | Further processing | Display<br>Command input |
| Transmission and reception<br>D/A conversion in TX e A/D conversion in RX | Beamforming in TX e in RX<br>Image Forming<br>Back-end processing | Further processing | Display<br>Command input |
| Transmission and reception<br>D/A conversion in TX e A/D conversion in RX<br>Beamforming in TX and in RX | Image Forming<br>Back-end processing | Further processing | Display<br>Command input |
| Transmission and reception<br>D/A conversion in TX e A/D conversion in RX<br>Partial beamforming in TX and in RX | Partia beamforming TX and in RX<br><br>Image Forming<br>Back-end processing | Further processing | Display<br>Command input |
| Transmission and reception<br>Beamforming in TX | A/D conversion in RX<br>Beamforming in RX<br>Image Forming<br>Back-end processing | Image Forming<br>Back-end processing<br>Further processing | Display<br>Command input |
| Transmission and reception<br>Beamforming in TX<br>Partial analogue beamforming in RX | A/D conversion in RX<br>Beamforming parziale in RX<br>Image Forming<br>Back-end processing | Image Forming<br>Back-end processing<br>Further processing | Display<br>Command input<br><br>Fig. 6 |

MULTI-USER SYSTEM FOR THE ACQUISITION, GENERATION AND PROCESSING OF ULTRASOUND IMAGES

BACKGROUND

Field

The present disclosure relates generally to a multi-user system for acquiring, generating and processing ultrasound images.

Description of Related Art

Typically, the steps of processing the receive signals acquired using the ultrasound probes, i.e., the electrical signals generated by the electroacoustic transducers of the set of transducers provided on each probe, as a result of capturing the reflection echoes of the ultrasonic pulses transmitted to an object under examination, include the following processes:

the calculation of the transmission timing, the generation of the digital transmission signals, the D/A (digital/analog) conversion of the transmission signals, the A/D (analog/digital) conversion of the received signals, the beamforming in reception, the subsequent operations generically defined in the technical field as "back end processing" and which include for example: I/Q data extraction from beamformed receive signals, combination of receive data related to temporally successive transmissions, envelope extraction of receive signals, signal compression and decimation, alternative processing to B-mode image generation (Doppler, CFM etc), image post processing activities, scan conversion, image filtering, image enhancement and other image optimization processing, image measurements, as well as advanced imaging modalities such as elastography, attenuation imaging and others.

All or most of these processing activities can be performed by a hardware/software combination in which the processing hardware is substantially traditional, such as a computer or a PC, and in which the processing steps are in the form of instructions encoded in a program that is loaded and executed by said hardware.

Such a dematerialization, at least partial, is already present in some diagnostic imaging devices, in which a dedicated configuration of the electronics processing signals acquired from sensors/detectors/antennas is replaced by processing units with a standard electronic configuration that is capable of executing and running one or a suite of programs in which instructions are encoded to make such processing unit and corresponding peripheral units capable of processing the acquired signals according to the intended processing steps. Thus, the various processing tasks are characterized and configured in the software code that the conventional hardware executes, effectively dematerializing the specific part of these tasks from the materialized part, i.e., the electronics.

Centralized command and/or control systems for a plurality of imaging devices are known, for example from patent EP1262786 by the same owner. Herein, there is provided a combination of multiple nuclear magnetic resonance imaging apparatuses whose control electronics are in the form of a processing unit that is provided with a communication unit with a communication network. A server is provided also connected to said communication network and has user interface peripherals of various types, one or more memories and in said server is loaded a program in which instructions are encoded to manage the control units of the individual apparatuses for acquiring images in nuclear magnetic resonance and to generate images from the data received from the scanners of the apparatuses for acquiring images in nuclear magnetic resonance and optionally perform further processing of said images. Typically in this configuration, wherein the MRI scanner, substantially the magnetic structure and the various transmitting and receiving coils, as well as the gradient coils and any additional operating organs is a structure that forms a patient housing compartment and requires the patient to remain stationary on a support, such as a chair, crib or the like.

The connection to the communication network of the communication units associated to the various MRI devices can be of wired type, using traditional network interfaces and protocols, without affecting the convenience of use of the devices.

In the case of ultrasound probes, these are moved and manipulated on the patient by the service personnel in charge and therefore the convenience of use is directly related to the constraints that the probe must have with the unit of image generation and the size of this same unit.

Although the provision of a cable of the type used in the networks is already a step forward in the greater convenience of handling the probe thanks to the low number of wires compared to those provided in traditional cables connecting the probes to the image generation units, a particularly advantageous solution involves the use of a communication between the ultrasound probe and the communication network of the wireless type, or wifi.

This type of solution is known for example from document US2015313578. In this document, a plurality of ultrasound probes each provided with a communication unit of wifi type transmits the reception signals collected during the scanning of a target under examination to a central server which is configured thanks to software so as to be suitable to perform the typical functions of the control and image generation units and/or processing of the images generated by traditional ultrasound scanners.

The ultrasound screen and the interface for data and/or commands input is in this case replaced by a multitude of display screens, preferably of the touch type, which are distributed in the environment dedicated to the execution of the acquisition of ultrasound images.

This solution solves in principle the problem of making the probe completely free from mechanical constraints and therefore to be manipulated and moved on the patient with the greatest ease and agility.

However, this system finds a limitation in the fact that especially when there is a large number of probes operating simultaneously on different patients, the system requires a considerable bandwidth and a high transmission speed. The two features are not unrelated, since when the bandwidth is reduced it is necessary to apply multiplexing processes or sharing of acquisition channels.

There are known attempts to integrate within the ultrasound probe some circuits intended to perform operations such as amplification, generation of waveforms of command of the transducers for transmission signals and/or processing of beamforming in transmission and/or reception known as beamforming. This integration is intended to reduce the amount of signals to be transmitted by providing part of the processing already in the probe itself.

In US2015313578, the image is divided into frames or tiles smaller than the overall image size and the data transmitted from the probe to the central unit and from the central unit to the display screen are only those tiles for which changes in the image represented in them have occurred.

However, this mode requires special image processing and routines to identify changes in the content of the various tiles at each new image frame.

A further limitation of the proposed solution at the state of the art consists in the fact that even if at the experimental and prototype level there is the possibility of creating a device actually working, this device is very far from being able to be used concretely in current medical practice and the development of a device mature for use still requires a very long time for a number of technical reasons that go beyond the mere limitation of bandwidth.

Typically, a generic probe for acquiring ultrasound images comprises a set of electroacoustic transducers, each of which emits ultrasonic waves when powered with an electrical excitation signal and further generates an electrical reception signal when an ultrasonic pulse or wave that may be generated by reflection of the ultrasonic waves emitted by the same transducer is engraved thereon. The transducer assembly is provided with at least one communication line with a processing unit by which each transducer provides reception signals to said processing unit, and a communication line by which electrical excitation signals produced by a generation unit for exciting each individual transducer to ultrasonic wave emission are transmitted to each transducer, which generation unit includes means for generating excitation signals and means for feeding said signals to said transducer assembly.

An ultrasound imaging system can be divided into a front-end (FE), an image former (IF) and the back-end (BE). The FE manages the hardware aspects of the transducer, the generation of transmission (TX) pulses, the reception of the analog signal (RX), and a switching matrix (SM) for the transmission (TX) and reception (RX) phases. The image former is responsible for beamforming, and sometimes this function is split between the IF image former and the FE front-end. The function of the Back-End is to enhance the images, convert them from acoustic scan grids to display grids, and then render and display said images.

Recently, IF and BE have often been combined in software using raw data directly.

This approach requires multiple high-speed, generally PCIe®-based communication channels to transfer raw data to a workstation equipped with a high-performance CPU and GPU.

The amount of data to be transferred from the FE Front-end to the BE Back-end is substantial and for example for a high-end 128-channel system, operating at 40 MHz sampling rate, encoded at 12 bits per sample, each TX transmit pulse event generates a raw data size of 2,212 MB for a 7.7 cm axial image at a sound speed of 1540 m/s. Considering a pulse repetition of e.g. 15,400 times per second as in ultrafast imaging, the data to be transferred is of the order of magnitude of 18.8 GB/s. Such orders of magnitude make it difficult or at least only theoretical to implement a system for ultrasound imaging, for example, like the one described in US2015313578.

SUMMARY

Problems are overcome and advantages are realized by illustrative embodiments described herein.

A multi-user system for acquiring, generating and processing ultrasound images is provided, said system comprising:

- a plurality of ultrasound probes configured to scan patients at predetermined examination sites and provided with a communication unit for transmitting the corresponding data to one or more processing units also provided with a communication unit;
- a plurality of display and/or user interface terminals provided in the vicinity of the examination sites and provided with a communication unit for transmitting to and receiving data from one or more of said processing units and/or one or more of said probes;
- a communication network connecting together the communication units of said probes, said display and user interface terminals and said one or more processing units;
- said probes and said display and/or user interface terminals each being identified by a corresponding ID, and
- said one or more processing units being configured to receive the scanning signals detected by each or at least one of said probes and to process said signals to generate ultrasound images and/or optionally only or also process said ultrasound images and to transmit said images and/or the outputs of said processing to one or more of said plurality of display and user interface terminals univocally associated with the probe that transmitted the data from which the image and/or the processing thereof was generated;
- in said processing units being loaded programs in which are encoded the instructions to receive data from each of said probes and to generate the corresponding images and/or to perform the corresponding processing, and/or to associate each probe to a predetermined patient and/or to a predetermined service person and/or to a predetermined display terminal and to receive from the user interface terminal possible commands and/or setting data, said instructions being executed by said central processing unit upon execution of said program.

BRIEF DESCRIPTION OF THE DRAWINGS

These and other features and advantages of example embodiments of the present disclosure will become more clearly apparent from the following description of some embodiments illustrated in the accompanying drawings wherein:

FIG. 6 shows by means of a graphic in the form of a table some different possible configurations of an ultrasound system according to embodiments herein and in particular according to FIG. 2 and corresponding variants in which the possible different subdivisions of the front-end, image forming, back-end and further processing processes of an ultrasound imaging system are shown, the process entries being to be interpreted as specific software loaded and executed by processing units provided in the probe, the local processing unit, the central processing unit and the display and user interface terminal.

DETAILED DESCRIPTION OF ILLUSTRATIVE EMBODIMENTS

Figure 1:
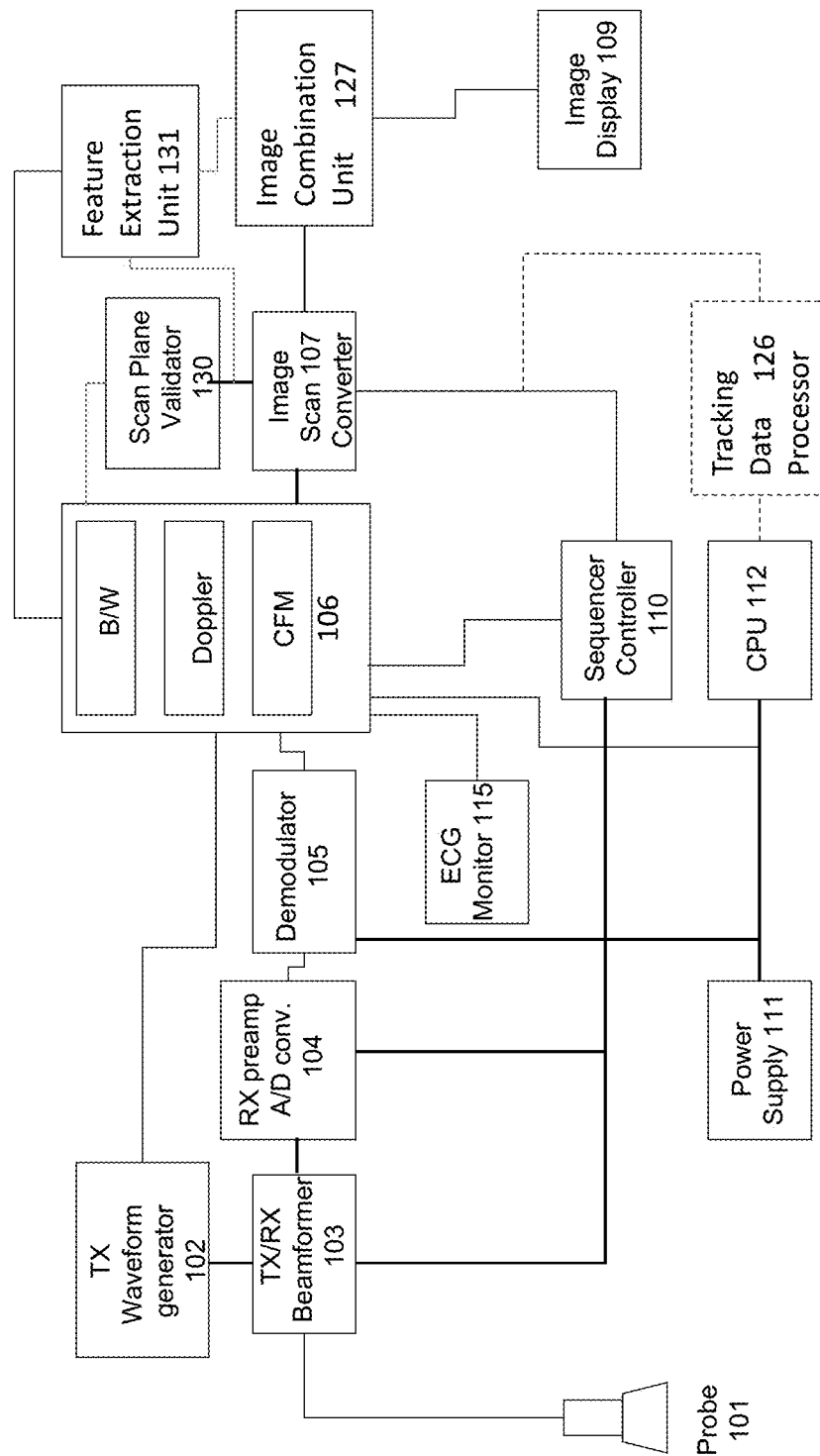
FIG. 1 shows a high-level block diagram of an ultrasound image acquisition system according to the state of the art.

FIG. 1 shows a high-level block diagram of a state-of-the-art ultrasound imaging system. Such a system is shown without any limiting purpose, but only for illustrative purposes to define an established state of the art, wherein the ultrasound system shown is combined into a single stand-alone device.

The probe 101 may include various transducer array configurations, such as a one-dimensional array, a two-dimensional array, a linear array, a convex array, and the like. The array transducers may be managed as a 1D array, a 1.25D array, a 1.5D array, a 1.75D array, a 2D array, a 3D array, a 4D array, etc.

The ultrasonic probe 101 is coupled via a wired or wireless connection to a beamformer 103. The term beamformer refers to a device for forming a beam of ultrasonic pulses, which pulses are each generated by one of the transducers of the array of transducers forming the probe. Since with respect to a point arranged within an area to be examined the distance of each of the transducers of the probe is different and considering the speed of the acoustic wave substantially constant in the region under examination crossed by the ultrasonic pulses to reach the said point, the times required for the various pulses generated respectively by one of the transducers of the probe, are different and to focus said pulses on the point under examination so that said pulses combine constructively it is necessary that the same arrive at the predefined point at the same time and possibly with the same phase. This process is typically performed not only in the transmission phase, but also in the reception phase. In fact, even in this case, the acoustic impulses reflected from a point inside the body under examination and for which it is assumed a substantially homogeneous transit speed in the said body under examination reach in different times the various transducers because of the different length of the path between each transducer and the point of reflection. In order to reconstruct the overall contribution of the reflected wave, it is therefore planned to realign temporally the contributions of the individual impulses received by the individual transducers to obtain their constructive combination.

As it will appear later there are several techniques of focusing in transmission and in reception that allow to reduce the computational burden of this process, both in terms of hardware needed and in terms of processing time for the formation of the beam of transmission and/or reception.

Thus, the beamformer 103 according to the state of the art comprises a transmit beamformer (TX) and/or a receive beamformer (RX) that are jointly represented by the TX/RX beamformer 103. The TX and RX portions of the beamformer may be implemented together or separately. The beamformer 103 provides transmit signals to the probe 101 and performs beamforming of the "echo" receive signals received by the probe 101 according to the intended mode of forming of the reception and/or transmission beams.

A TX waveform generator 102 is coupled to the beamformer 103 and generates transmission signals that are provided by the beamformer 103 to the probe 101. The transmission signals may represent various types of ultrasound TX signals, such as those used in connection with B-mode imaging, Doppler imaging, color Doppler imaging, pulse inversion transmission techniques, contrast-based imaging, M-mode imaging, and the like. Additionally or alternatively, the transmission signals may include single or multi-line transmission, transmission pulses may be focused on single lines or may be focused to extend over larger areas or an entire region of interest (referred to in technical jargon as ROI), e.g., in the form of plane waves, or transmission pulses may be unfocused and consist of pulses transmitted from a single point i.e., from a single transducer of the transducer array at a time or from a selected subset of transducers or even from all transducers of the probe transducer array that are controlled in transmission so as to generate a pulse or wave or sequence of transmission pulses configured as if they were emitted from a common physical point of view or from multiple individual points i.e., transducers or from multiple subgroups of transducers.

The beamformer 103 performs beamforming on received echo signals to form receive echo signals derived from receive signal contributions received from individual transducers, in connection with the locations of pixels distributed in the region of interest. For example, in accordance with certain embodiments, transducer elements generate raw analog receive signals that are provided to the beamformer. The beamformer adjusts delays to focus the receive signal along one or more selected receive beams and at one or more selected depths within the region of interest (ROI). The beamformer adjusts the weighting of the receive signals to achieve the desired apodization and profile. The beamformer applies weights and delays to the receive signals of the corresponding individual probe transducers. The delayed and weighted receive signals are then summed to form a coherent receive signal.

The beamformer 103 includes (or is coupled to) a preamplifier and/or A/D converter 104 that digitizes the receive signals at a selected sampling rate. The digitizing process may be performed before or after the summation operation that produces the coherent receive signals. The beamformer also includes (or is coupled to) a demodulator 105 that demodulates the receive signals to remove the carrier waveform. Once the receive signals are demodulated and digitized, complex receive signals including components I,Q (also referred to as data pairs I,Q) are generated. The data pairs I,Q are stored in memory as image pixels. The data pairs I,Q, which define the image pixels for the corresponding individual positions along the corresponding lines of sight (LOS) or sight lines. A collection of image pixels (e.g., data pairs I,Q) are collected over time and saved as 2D frames and/or 3D volumes of image data. The image pixels correspond to tissues and other anatomy within the ROI.

Optionally, a dedicated sequence/timing controller 110 may be programmed to manage the timing of the acquisition, which may be generalized as a shot sequence aimed at selecting reflection points/targets in the ROI. The sequence controller 110 manages the operation of the TX/RX beamformer 103 in connection with the transmission of ultrasonic beams and the measurement of image pixels at individual LOS locations along the lines of sight. Sequence controller 110 also manages the collection of receive signals.

One or more processors 106 and/or CPU 112 perform various processing operations as described herein.

For example, the processor 106 executes a B/W module to generate B-mode images. The processor 106 and/or the CPU 112 executes a Doppler module to generate Doppler images. The processor executes a color flow module (CFM) to generate color images. The processor 106 and/or CPU 112 may implement additional ultrasound imaging and measurement operations. Optionally, the processor 106 and/or CPU 112 may filter the first and second displacements to eliminate motion-related artifacts.

An image scanning converter 107 performs image pixel scanning conversion to convert the image pixel format from the coordinate system of the ultrasound acquisition signal path (e.g., the beamformer, etc.) and the display coordinate system. For example, the scan converter 107 may convert image pixels from polar coordinates to Cartesian coordinates for frames.

A cine memory not illustrated in detail stores a temporal sequence of frames. The frames may be stored with formats in polar coordinates, Cartesian coordinates, or another coordinate system.

An image display 109 displays various ultrasound information, such as frames and measured information according to the embodiments herein. The image display 109 displays the ultrasound image with the region of interest indicated.

A control CPU module 112 is configured to perform various tasks such as user/interface implementation and general system configuration/control. In the case of an all-software implementation of the ultrasound signal path, the processing node usually also houses the functions of the control CPU.

A power supply circuit 111 is provided to power the various circuits, modules, processors, memory components, and the like. The power supply 111 may be an AC power source and/or a battery power source (e.g., in connection with portable operation).

According to the present embodiment and by way of example, the processor 106 may be associated with or possibly also comprise an ECG monitoring module that receives signals from an ECG (not shown in detail) and allows for combining image acquisition with ECG signals according to different variations of known ECG signal synchronized image acquisition techniques.

The purpose of example embodiments of the present disclosure is to provide a system of the type described at the beginning, in which it is possible to overcome not only problems related to the bandwidth of the wifi channels and the speed of transmission of the signals between the probe and the processing unit and/or the said processing unit and the display terminals, as well as between the user interfaces and the said processing unit, but also to overcome drawbacks related to the actual possibility of concretely realizing a device that is mature for the market and its use.

According to a first aspect of example embodiments of the present disclosure, the above problem is solved by providing for a distributed structure of the processing unit, comprising at least two, preferably three, optionally at least four or more processing units which are each integrated respectively in the probe and/or in an optional local processing unit associated with one or more patient stations and dedicated to a single probe or a partial number of probes and possibly positioned in the immediate vicinity of said one or more patient stations and/or in a remote central processing unit which is associated with all and/or at least some of said probes and/or said local processing units, and/or with one or more of said plurality of display terminals and user interface,
    said processing units being communicating with each other;
    and being the processing steps of the receiving signals of said probe/s divided on said processing units in such a way that one or more of said processing units performs only a portion of the processing steps,
    loading in the working memories of said processing units and having said processing units execute programs in which are coded the instructions to make said operating units capable of executing the processing steps of the part of the processing steps attributed to them.

In particular, there is provided a processing program in which are encoded the instructions to make said one or more processing units capable of executing each all or only part of the processing steps selected from the following list:
    calculation of transmission timing, generation of digital transmission signals, D/A (digital/analog) conversion of transmission signals, A/D (analog/digital) conversion of received signals, beamforming in reception, subsequent operations generically defined in the technical field as "back end processing" such as, for example, the extraction of I/Q data from beamformed reception signals, the combination of reception data related to temporally successive transmissions, extraction of the envelope of the receive signals, compression and decimation of the signal, alternative processing to B-mode image generation, Doppler, CFM and other modalities, post processing activities on the image, scan conversion, image filtering, image enhancement and other optimization processing on the image, measurements on the image, as well as advanced imaging modalities such as elastography, attenuation imaging and combinations of one or more of the above listed steps.

According to an embodiment, the one or more probes and/or the one or more local processing units and/or the one or more central processing units and/or the one or more display and/or user interface terminals may communicate alternatively or in combination by means of a selection of the communication mode via a wired connection and/or a wireless connection.

According to yet another feature, it is possible to provide a local unit associated with a group of patient workstations, for example two or more patient workstations, a probe being provided for each workstation and/or for two or more workstations of said group.

Similarly, it is possible to provide a central processing unit operating in combination with one or more groups of patient stations, i.e., probes and/or local processing units.

Various configurations of the system are possible according to the most general combination above.

According to one embodiment, a configuration of the system comprises.
    at least one of the probes is connected to local processing units via analogue cable;
    the D/A conversion in transmission (TX), A/D conversion in reception (RX) is performed on a local processing unit and the beamforming in transmission and/or reception (TX/RX) and further processing according to one or more of the above steps on a central processing unit.

An implementation variant alternatively provides that
    at least one of the probes is connected to local processing units via analog cable;
    D/A conversion in transmission (TX), A/D conversion in reception (RX) and beamforming in transmission and/or reception (TX/RX) on a local unit and further processing on a central processing unit.

According to a further embodiment a configuration of the system comprises.
    at least one probe is wired or wirelessly connected to a local processing unit with a digital connection;
    the D/A conversion in transmission (TX), A/D conversion in reception (RX) is performed on the probe and the beamforming in transmission and/or reception (TX/RX) and back-end processing on a local processing unit and the further processing according to one or more of the steps more listed above on a central processing unit.

An implementation variant alternatively provides that
at least one probe is wired or wirelessly connected to a local processing unit with a digital connection;
D/A conversion in transmission (TX), A/D conversion in reception (RX) and beamforming in transmission and/or reception (TX/RX) are performed on the probe and back-end processing on a local processing unit and further processing according to one or more of the above steps on a central processing unit.

Still another variant of execution alternatively provides that
at least one probe is wired or wirelessly connected to a local processing unit with a digital connection;
the D/A conversion in transmission (TX), A/D conversion in reception (RX) are performed on the probe, while the beamforming in transmission and/or reception (TX/RX) are performed partly on the probe and partly on a local processing unit and the back-end processing on a local processing unit and the further processing according to one or more of the steps more listed above on a central processing unit.

A further embodiment provides that
at least one probe is connected to a local processing unit by means of a cable and an analogue or digital connection;
the transmit signal generation and transmit beamforming are performed on the probe, the receive A/D conversion (RX) and receive beamforming are performed on a local unit, and the back-end processing and further image processing are performed on a local or central unit.

An alternative implementation variant is that
at least one probe is connected to a local processing unit by cable and with an analogue or digital connection;
the transmit signal generation, the transmit beamforming and the receive beamforming, partially analogue are performed on the probe, the receive A/D conversion (RX) is performed on a local unit, while further beamforming steps, back-end processing and further image processing are performed on local or central unit and some further processing steps are performed only on a central unit.

An implementation variant may provide that the local processing unit/s are omitted and that functions performed by the local processing unit/s according to any of the above described forms and implementation variants are performed by the probe and/or a central processing unit, or that said functions are divided between the probe and said one central processing unit.

According to one embodiment, for example, the probe may comprise a DAC and/or ADC conversion unit.

Alternatively, different variants are possible according to which the probe may comprise a DAC/ADC conversion unit and a beamforming unit in transmission and/or reception, or alternatively a DAC/ADC conversion unit, a transmit and/or receive beamforming unit and back-end processing units, or according to yet another alternative, a beamforming unit in transmission and/or reception, one or more units of back-end processing and a scan converter, as well as optionally units of execution of further processing of the images, being in this case transmitted to a central processing unit only the ultrasound (echographic) images already formed.

Although this configuration of the system that provides a plurality of processing units on which are distributed at least part of the different processing tasks of the signals of reception and/or transmission, may help in a reduction of data to be transmitted between the probes, local and central processing units and terminals display and/or user interface and then in a limitation of bandwidth occupation, especially for solutions involving a connection by means of wireless protocols, it is important to be able to combine with one or more of the above mentioned executive forms and executive variants expedients that can further limit the amount of data transmitted between the probe(s), the local processing unit(s) the central processing unit(s) and the display and/or user interface terminal(s).

According to an embodiment that can be provided in any combination or sub-combination with one or more of the above-described embodiments and variants of the present disclosure, the system further provides for applying alternately with each other and/or, when possible, also in any combination with each other one or more data quantity reduction processes selected from the following list:

Adaptive temporal decimation of data, according to a predefined bandwidth, adjusting the sampling frequency according to the Nyquist limit (twice the maximum frequency for RF data, maximum-frequency-minimum for IQ data);

Use of a subset of receive transducers, calculated based on the maximum receive aperture actually used to combine the signals for a given transmission;

Subsampling, periodic or aperiodic, in the time domain or in the receive channel domain or both and use of compress sensing techniques for image reconstruction based on sparsity priorities in the image domain or in a transformed domain such as Fourier transform, k-space, wavelet;

Subsampling, periodic or aperiodic, in the time domain or in the receiving channel domain or both, and use of machine learning techniques for reconstruction of missing data;

Subsampling by reducing the number of data by multiplying the received signals by a matrix with fewer rows than the number of columns;

Use of advanced beamforming techniques that allow to obtain images of equal or similar quality compared to standard line-by-line beamforming, reducing the number of transmissions and thus the amount of data required to form a frame, such as those in the following list: multiline receive beamforming, synthetic transmit beamforming (STB), retrospective transmit beamforming (RTB), synthetic aperture imaging, plane wave or diverging wave beamforming;

combination of beamforming based on synthetic aperture or plane wave or diverging wave beamforming, with a reduction in the number of transmissions and with a machine learning algorithm that maps low quality images obtained with a limited number of insonifications, onto images that reproduce the characteristics of high quality images that would have been obtained with a higher number of insonifications.

Two-stage beamforming or microbeamforming in which a portion of the beamforming is performed on the probe on distinct groups of transducers, thus reducing the number of communication channels between probe and apparatus and consequently the data transfer rate, and in which the further portion of the beamforming is performed by a local and/or central processing unit, being the instructions for the execution of said processes encoded in a corresponding program which is loaded and which is executed by the processing unit of the probe(s) and/or the local unit(s) and/or the central unit(s) and wherein the execution of said program configures said processing units and associated peripherals to perform the functions of the above one or more processes for reducing the amount of data to be transmitted between the said probe(s) and/or the said local processing unit(s) and/or the said central processing unit(s).

Retrospective Transmit Beamforming e Synthetic Transmit Beamforming (STB)

Regarding the beamforming protocol called Retrospective Transmit Beamforming, this is described for example in document EP3263036 by the same holder. This document is incorporated herein by reference and is part of this description.

For completeness, in summary, RTB technology is a transmission focusing technology that achieves dynamic focusing by performing the transmission focusing operation retrospectively.

In Retrospective Transmit Beamforming (RTB), multiple receive beams are generated following an ultrasound transmission beam event. Ultrasound images are composed of a set of lines along each of which the imaging system acquires image data until a complete frame is scanned.

According to this technique, the transmission beam is generated with a width that encompasses, i.e., covers, the area over which multiple receiving lines are distributed. Generally, this can be achieved by transmitting from a small transmission aperture, for example by transmitting using fewer elements of a transducer array than the total number of transducers in the array.

After transmission, echoes are received which are focused along each line of the lines falling within the transmitted beam width. Focusing is achieved by delaying and summing up together the received echoes from the transducer elements of the receiving aperture so that only the contributions from the signals that are coherent along each different position of the lines are used to generate the image of each line between the lines falling within said transmission beamwidth.

In order to scan the entire region of interest (ROI) of the image and acquire all lines that fall within said region of interest and are required to generate said image, additional transmission beams are transmitted by shifting the transmission aperture laterally in one direction relative to the transmission aperture of the previous transmission event. The lateral shifting is performed such that the two adjacent transmission apertures overlap, so that at least some of the receiving lines fall within the width of a first transmission beam also fall within the width of at least one or more of the following transmission beams whose aperture has been progressively shifted laterally relative to the transmission aperture of the first transmission beam.

Accordingly, depending on the transmission aperture, i.e., the number of lines enclosed by the width of the transmission beam and the step of lateral displacement of the transmission aperture for each successive transmission event, the image data along a predetermined line of sight are formed from the mutually aligned contributions of the receiving beams along the same receiving line and acquired in each of the transmission events and which contributions are combined together.

Transmission and reception continue in this manner through the area of the image region of interest until the entire area has been scanned. Whenever the maximum number of receive lines has been acquired for a given line position, the receive lines are processed together to produce a line of image data at that position.

It is worth noting here that, the reduction in the amount of data to be processed in the probe and/or the local unit and/or the central unit depending on the chosen configuration by which the various processing of the transmit and receive marks are distributed on the probe, the local unit and the central unit, also depends on an accurate selection of the area of interest, i.e., the so-called ROI.

A method of RTB is described in EP3263036, which involves the following steps:

(a) transmitting a plurality of transmission beams from a probe comprising a set of transducers, each transmission beam being centered at a different position along said set of transducers and each transmission beam having a width or aperture comprising a plurality of laterally spaced line-of-sight positions, each width or aperture of the transmission beam at least partially overlapping at least the width or aperture of the immediately adjacent transmission beam or more laterally spaced transmission beams;

(b) receive echo signals with said set of transducers;

(c) processing echo signals received in response to a transmission beam to produce a plurality of echo signal reception lines at laterally spaced positions of the reception lines within the width or aperture of the transmission beam;

(d) repeating the receiving step (b) and the processing step (c) for the additional transmission beams of the plurality of transmission beams transmitted in step (a);

(e) equalize the variance of the phase shift between the receiving lines at a common line position and resulting from transmission beams of different positions of the transmission beams;

(f) combine receiving line echo signals resulting from different transmission beams that are spatially correlated to a common line position to produce image data; and (g) producing an image using the image data;

and wherein step e) of equalizing the phase shift is performed concurrently with processing steps c) and d).

According to an embodiment of the present disclosure, for each insonification, i.e., for each transmission of a transmission beam with a certain aperture, the received echoes are processed by a series of beamformers, each relating to a different line of sight, each beamformer being characterized by a series of dynamic delays and, optionally, by a series of apodization weights, which are different for each beamformer.

According to one executive form, the delays are given by the summation of the focus delays and RTB delays, which are the phase shifts between the wavefronts of different transmission beams centered on different transmission lines at the focal points along a receiving line having a certain line position.

According to one execution form after beamforming, each line of sight is stored in a buffer and together with subsequent insonifications, the receiving lines corresponding to the same line positions are summed consistently to produce a final focused line with uniform spatial resolution.

According to yet another implementation form for each receive signal along a receive line position, focus delays and phase shift equalization delays are applied to the receive signal contributions of the transducers prior to their summation.

Document EP3263036 further describes is provided an ultrasound system comprising:

an ultrasound probe comprising an array of transducers that transform electrical input signals into acoustic transmission signals and transform acoustic echo signals into electrical reception signals;

a transmission beamformer feeding transducer drive signals according to an RTB-type beamforming protocol in which the transducers are commanded to transmit a plurality of transmission beams, each transmission beam being centered at a different position along the extent of the transducer array and each transmission beam having a width or aperture comprising a plurality of laterally spaced line positions, each transmission beam width or each aperture at least partially overlapping at least the width or aperture of the immediately adjacent transmission beam or laterally spaced transmission beams;

the transmission beamformer including a memory configured to store time delays to synchronize the contributions of the transmission signals of the transducing elements of the array according to said transmission pattern;

a receive beamformer including a receive signal processing unit configured to process echo signals received in response to a transmit beam to produce a plurality of receive lines of echo signals at laterally spaced apart receive line positions within the width or aperture of each of said plurality of transmission beams;

a focus and phase equalization delay module that applies corresponding focus and phase shift equalization delays to each receive signal contribution from each transducer or receive channel to realign the arrival time of the receive signal contributions to the transducers of the set of transducers from each reflecting or focusing point and to equalize the variance of the phase shift between the signals along a receive line for each reflecting or focusing point at a common line position, said signals along the receiving line resulting from transmission beams having different positions based on the stored delay and phase shift values between the receiving lines with respect to a common line;

A summing device for summing for each receive line position within the width or aperture of a transmission beamformer the receive signal contributions of the transducer elements from the focal points on said receive line position, which contributions are realigned and equalized relative to the phase shift by applying corresponding focus delays and corresponding phase shift equalization delays;

a memory connected to the receiving beamformer and configured to store said plurality of receiving lines of echo signals processed along a common receiving line position and resulting from transmission beams having different positions;

a line combining module connected to said memory and configured to combine receiving line echo signals from different transmission beams that are spatially relative to a common line position to produce image data along said line position;

an image generating unit producing an image using said line image data, and wherein said transmitting beamformer, said receiving beamformer, said focus delay and phase equalization module, said summing unit, said memory and said line combination module, are integrated into the probe case, while the image generating unit is integrated within the server processing unit.

According to an embodiment, the system further comprises a precomputed table stored in a memory. The precomputed table includes actual arrival times of the receive signals relative to a predetermined reflection point. The system further includes a processor configured to calculate actual arrival times of the receive signals relative to a predetermined reflection point. In accordance with the executive forms, the processor is configured to calculate the focus delay for each of the receive signals and the phase shift between the receive lines at a common line position resulting from the transmission beams of different transmit beam positions and to add the focus delays of each of the receive signals relative to a predetermined reflection point with the corresponding phase shift and apply the result of said sum as a combined delay parameter to said receive signals.

According to an embodiment, the memory is configured to store the program instructions and the circuit includes a processor that, when the program instructions are executed, is configured to apply the combined delay resulting from the sum of the focus delays and phase shifts to the receive signals. Optionally, the system further includes a processor configured to provide parallel multiline receive (PMR) beamforming in connection with single display lines acquired in parallel simultaneously with a focusing function.

According to an embodiment herein, the beamformer is a multiline beamformer comprising a multiline processor for each receiving line that falls within said aperture or said width of each transmission beam centered on a certain position of the transmission line.

According to an embodiment, each multiline processor includes a number of channels corresponding to the number of probe channels or transducer elements.

The beamforming technology referred to in the industry as Synthetic Transmit Beamforming (STB) is essentially analogous to Restrospective Transmit Beamforming, but differs from the latter in that it does not apply in receive beamforming the corrections to delays as a function of distance between the transmission line and the receive line and that take into account the curvature of the transmission wavefront.

Synthetic Aperture Imaging

The beamforming protocol called Synthetic Aperture Imaging consists of a beamforming process whereby echo reception signals from transmission pulses of individual pairs of elements are synthesized to reconstruct beam formation and focusing, based on the linear superposition rule. The operating principle of a Synthetic Aperture Imaging system is that it transmits an ultrasonic wave in turn from each small group of the transducer elements forming the transducer set of a probe, receives a signal using all possible transducer elements of said set or a set of receiving transducers then reconstructs the image by a weighted sum of all demodulated receiving signals.

This beamforming protocol allows dynamic focusing in both transmission and reception without repeating the transmission process with all transducer elements of the transducer array for each focal zone. This reduces the amount of data and at the same time the computational burden for the beamforming calculation, e.g. according to a "delay and sum" process. In addition, the Synthetic Aperture Imaging process significantly reduces the hardware complexity for system implementations.

A description of the above protocol can be found in the publication J. A. Jensen, S. I. Nikolov, K. L. Gammelmark, and M. H. Pedersen, "Synthetic Aperture Ultrasound Imaging," Ultrasonics, vol. 44, pp. e5-e15, 2006.

US2014058266A1 also describes a specific application based on Synthetic Aperture Imaging.

A further description of the beamforming protocol called Synthetic Aperture Imaging is contained in the paper "Synthetic Aperture and Plane Wave Ultrasound Imaging with Vesrsal ACAP" incorporated herein by reference and published and available at the web address https://www.xilinx.com/ . . . /white papers/wp520-sa-pw-imaging.pdf.

Plane Wave and Diverging Wave Ultrasound Imaging

This technology involves the use of plane or divergent acoustic waves in transmission, while in reception is essentially performed a recombination of the image data obtained from each individual transmission.

The Plane Wave Beamforming technology is described in the document "Synthetic Aperture and Plane Wave Ultrasound Imaging with Vesrsal ACAP" incorporated herein by reference and published and available at the web address https://www.xilinx.com/ . . . /white papers/wp520-sa-pw-imaging.pdf.

A particular execution form involves performing a multiple transmission with plane or divergent waves whose propagation direction is oriented at different angles to each other.

Receive beamforming can be performed using a traditional "Delay and Sum" process, or it is possible to use a receive beamforming process called "back propagation".

The technology of beamforming using the "Delay and Sum" protocol is a standard technology widely known to the branch engineer and is considered to be included in this description because it is contained in the branch engineer's basic technical knowledge.

The technique of beamforming by means of "back propagation" is described, for example, in U.S. Pat. Nos. 5,628,320 and 5,720,708, which include a detailed and comprehensive description of the theory and method of back propagation and whose information content is intended to be incorporated by reference into this description.

According to a summary relating to the general technical concepts of this technology, the acquisition is performed according to the following steps:
  (a) at least one ultrasonic pulse is generated by activation of a plurality of electroacoustic transmission transducers belonging to a predetermined array of transmission transducers, said pulse being emitted in the direction of an examination area of a body under examination;
  b) said transmission transducers being activated in a uniform manner such as to generate an array of unfocused or partially focused scan lines;
  (c) at a line, or a curved line, or a plane or a reference surface, the time domain signal consisting of the transmission impulse reflected back from the structure of the zone under examination is received by each of the receiving transducers of a set of receiving transducers possibly consisting of the same transmitting transducers;
  (d) a back propagation calculation of the reception signal of each reception transducer is performed to at least one straight or curved line or plane or penetration surface in the area under consideration, which straight or curved line or plane or penetration surface is provided at a certain distance from the straight or curved line or plane or penetration surface and corresponding to a predetermined depth of penetration of the transmission pulse in the area under consideration;
  (e) said signals obtained from the back propagation calculation and relating to each receiving transducer are combined with each other and processed into control signals of a display monitor.

The system provides for a limited number of processing channels which is less than the number of receiving electroacoustic transducers being made up of an integer submultiple of the number of receiving transducers), while for each image detection along an entire scan plane or part thereof it is provided to perform a number of transmission steps in which all the transmission transducers are activated, which number is at least equal to the inverse of the submultiple of expected receive channels, being, for each transmission step, connected to the receive channels a different group of receive transducers of the set of transducers, which groups of receive transducers comprise a number of receive transducers equivalent to the number of expected processing channels.

A further alternative envisioned in conjunction with a Plane Wave Beamforming protocol involves the use of an algorithm for combining image data related to individual plane wave pulse emissions in order to generate the final image referred to as the Convolutional Compounding Algorithm. An example of this algorithm is described in the paper Sparse convolutional plane-wave compounding for ultrasound imaging, Baptiste Heriard-Dubreuil, Adrien Besson Frédéric Wintzenrieth, Jean-Philippe Thiran and Claude Cohen-Bacrie, [Proceedings of IUS 2020], Conference 2020 IEEE International Ultrasonics Symposium (IUS 2020), Las Vegas, US, Sep. 6-11, 2020.

Compressed Delay-And-Sum Beamforming

The technique called Compressed Sensing is based on the structure of signals in order to reduce the number of samples needed to reconstruct a signal, compared to Nyquist's law. The basic principle of CS is to measure only a few fundamental coefficients of a compressible signal and then reconstruct it through an iterative process of optimization.

A method and an imaging system using beamforming technology using a Compressed Sensing technique are described in document EP2660618A1 which is incorporated by reference into and made part of this description.

In summary, and for the convenience of reading the present description, a method for reconstructing an image, e.g., from image data comprising receive signals generated by electroacoustic translators as a result of receiving echoes of transmitting ultrasonic signals comprises the following steps:
  (a) transmitting ultrasonic pulses into a body under examination for generating echo signals;
  (b) acquiring image data from the receiving signals of electroacoustic sensors of an ultrasound imaging probe pe caused by echo signals, and wherein said receiving signals are acquired by pseudo-random sub-sampling;
  (c) reconstructing said one or more images by a non-linear iterative algorithm for minimizing an optimization functional containing one or more terms relating to the sparsity of the image data in one or more predetermined domains, with a fidelity term constrained to the acquired image data.

A specific embodiment further contemplates that two or more sets of image data are acquired, each set being acquired with a different subsampling mode and/or a different acquisition mode, for the formation, identification and suppression of inconsistent artifacts.

It appears evident that the technique of transmission beamforming, i.e., image reconstruction by Compressed Sensing can be envisaged in combination with traditional beamforming techniques, such as the "Delay and Sum" technique and also with beamforming techniques such as RTB, STB, Plane wave or divergent wave Imaging or even Synthetic Aperture Imaging, since these techniques however require sampling of the receiving signals.

Micro-Beamforming or Sub-Array-Beamforming

According to a method for ultrasound imaging referred to as micro-beamforming, electroacoustic transducers of a probe set are grouped into subsets, and the probe includes a switch/switch that connects each subset and the processing system. In the micro-beamforming operation, the signals received from the transducers included in a subset are summed together to generate a common subset signal, and the set of subset signals corresponding to a particular receive beamforming scheme is defined using a signal that controls the output of the switch/smother. Therefore, the amount of signal that must be transferred between the probe and the processing unit is reduced compared to traditional techniques.

Part of the beamforming takes place in the probe itself, i.e., the generation of the combined receive signals of each subset, while the combination of the receive signals of different subsets is performed in the processing unit of the ultrasound system separate from the probe. It seems clear that therefore the number of channels between the probe and the ultrasound processing apparatus is significantly reduced compared to traditional techniques.

A specific implementation form is described in document US20080262351A1 which is incorporated into this description by reference.

It appears evident that also in this case, the various alternatives mentioned above and which allow to modify the amount of data based, for example, on particular sampling techniques are applicable to this technology, as well as in the same way and in combination with the different sampling techniques also the different beamforming techniques described above, in particular, RTB, STB, Synthethc aperture Imaging, Plane Wave Imaging, Divergent Wave Imaging, Standard Delay and Sum, etc.

According to still an executive form that can be predicted in combination with one or more of the preceding executive forms and variants, machine learning techniques can be applied for the beamforming step in receiving.

These machine learning or deep learning techniques can be used to reconstruct image data with some quality even in the presence of a small number of transmissions.

Examples of these techniques are described in the papers "A Deep Learning Approach to Ultrasound Image Recovery", Dimitris Perdios, Adrien Besson, Marcel Arditi, and Jean-Philippe Thirany, 2017 IEEE International Ultrasonics Symposium (IUS) or "CNN-Based Image Reconstruction Method for Ultrafast Ultrasound Imaging", Dimitris Perdios, Manuel Vonlanthen, Florian Martinez, Marcel Arditi, and Jean-Philippe Thiran, IEEE Transactions on Medical Imaging (Volume: 40, Issue: 3, March 2021), Page(s): 1078-1089, which are incorporated by reference.

The use of image reconstructions using Artificial Intelligence algorithms has been known for decades in the field of Imaging.

An embodiment that can be contemplated in any combination or sub-combination with the above-described data reduction techniques and that involves the use of Machine Learning algorithms can contemplate the use of such algorithms to reduce and better define the size of an ROI with reference to a target of interest present in the body under examination and/or alternatively or in combination with the definition and choice of scanning planes.

With respect to managing communication between two or more probes and/or two or more local processing units and/or at least one central processing unit and/or one or more display and user interface terminals, an embodiment of the present disclosure provides that, in combination with any of the preceding embodiments or variations thereof, each probe is univocally associated with an identification code that is transmitted to the central processing unit, and each display and/or user interface terminal is also associated with a unique identification code that is transmitted to the central processing unit, said central processing unit being configured to univocally associate said probe with at least one display and/or user interface terminal.

According to yet another feature of the present ultrasound system, the probe and/or display and user interface terminal are provided with spatial localization systems, wherein the central processing unit comprises a virtual map of the area in which the probes and/or display and/or user interface terminals are disposed and a position determination unit for the probes and/or display and/or user interface terminals with reference to said virtual map, which position determination unit automatically associates a probe with at least one display terminal according to the relative distance between them and the absence of obstacles that make it impossible to directly view said terminal from the position of the probe, the terminal closest to said probe being associated with the probe.

According to an implementation variant, the unique association between the probe and the display terminal and/or user interface may occur directly between said probe and said terminal by direct communication of mutual positions and mutual identification codes, the probe and/or said terminal providing for transmitting the association condition to the central unit for displaying images generated by the data acquired by the probe on the terminal associated therewith and/or for transmitting user input to the probe and/or the central processing unit.

An implementation variant may provide for a user interface terminal in the form of a display screen and/or in the form of one or more buttons also on the probe itself, the display screen being intended to display information about the probe produced by the probe itself and/or information transmitted by the central unit and/or the display and/or user interface terminal and the input buttons being intended to transmit commands and/or settings to the units integrated in the probe itself and/or to the central processing unit and/or also directly to the display and/or user interface terminal associated with the probe.

According to still a further executive form which can be provided in combination with one or more any of the previous executive forms, the ultrasound system provides a module for encoding images generated by the central unit for generating and/or processing images in the form of video files, said central unit being provided with a streaming module for streaming transmission of the ultrasound images to the display terminal.

According to a further feature, the central image generation and/or processing unit further comprises a module for combining with said ultrasound images a graphical user interface and encoding said combination in the form of a video signal, as well as streaming said video signal by means of a streaming transmission module.

An implementation form comprises an ultrasound system of the type according to one or more of the preceding implementation forms with a multimedia information distribution system comprising:
- a video processor that generates a sequence of video frames of at least the ultrasound diagnostic images of a sequence of ultrasound diagnostic images;
- a video encoder that encodes the sequence of ultrasound images in the form of a video file;
- a streaming multimedia module that receives said video file and generates a real-time stream of the sequence of video frames encoded in said video file;

a web server that provides access to the real-time stream of video frames upon request of a remote client to access said video file.

According to a further feature, the display and/or user interface terminals comprise client units comprising, respectively:

A processing unit running a web browser and/or a media player executed by said processor or a dedicated graphics processor;
input devices for generating an access request;
a bidirectional communication unit for sending the access request to a web server and for connecting to the web server and receiving the video.

According to a further executive form the system according to one or more of the above executive forms may comprise a sound processor for generating audio files and a multimedia editor for combining digital acoustic data to video frames generating multimedia data, said multimedia data being encoded as a multimedia file and is sent to the multimedia streaming module.

Still according to a possible embodiment in combination with one or more of the preceding embodiments, the system may further comprise a text processor to transform digital alphanumeric information into video frames, said video frames being fed to said multimedia editor which is configured to combine said alphanumeric information (text information) with video frames representing ultrasonic images and acoustic data and generate combined multimedia data fed to the multimedia encoder for generating multimedia files.

A further embodiment of said ultrasound system according to one or more of the preceding embodiments, may further comprise a GUI image processor for transforming the GUI image into GUI video frames, said GUI video frames being fed to said multimedia editor which is configured to combine said GUI video frames with video frames representing ultrasound images and/or video frames representing textual information and/or acoustic data and generate combined multimedia data fed to the multimedia encoder to generate multimedia files.

A further embodiment of said ultrasound system according to one or more of the preceding embodiments is provided with an access control unit configured to receive access rights certificates and validate said access rights certificate by comparing in a comparison unit said access rights certificates with a database of registered access rights certificates stored in a memory and allowing access to the web browser of a remote client unit to the multimedia streaming module.

In this case, the access rights being constituted, for example, by the probe and/or display terminal and/or user interface identification codes associated with each other and possibly also in combination with enabling credentials of the system user, such as the physician or other relevant personnel.

In an embodiment, the access right certificates are correlated with selection parameters of the information available to the holder of said certificate, said selection parameter being recorded in the access right certificate database and the access right controller sending said selection parameter to a data content controller driving a data selection unit that drives the multimedia data editor to combine only the multimedia data related to the information available to the corresponding access right certificate.

According to still a further embodiment that may be provided in any combination with one or more of the preceding embodiments, the system may comprise a graphical banner generator for generating banners to cover or blur a display area in which information not available for a specific access right certificate is displayed, said graphical banner generator feeding the banner image to the media data editor for combining said banner image with one or more of said camera video frames and/or said GUI video frames and/or video frames representing the ultrasound images and/or video frames representing the textual information.

According to still one embodiment of the present ultrasound system according to one or more of the previously described embodiments, said system is provided with a controller that measures the frame rate of the frames displayed on the client display, said controller driving a unit for discarding video frames from the multimedia data stream configured to discard video frames from said multimedia data stream and optionally associated acoustic data when the frame rate of the displayed frames falls below a certain threshold, said input interface for setting said threshold also being provided.

According to a further feature, the ultrasound system according to one or more of the preceding embodiments comprises a comparator group that compares each successive video and/or acoustic frame with the preceding one and discards from the multimedia file to be generated the video frames that are identical with the preceding ones while retaining in the video file only the video frames that are different from the preceding ones. These and other features and advantages of example embodiments of the present disclosure become more clearly apparent from the description of some embodiments illustrated in the accompanying drawings wherein:

FIG. 1 shows a high-level block diagram of an ultrasound image acquisition system according to the state of the art.

Figure 2:
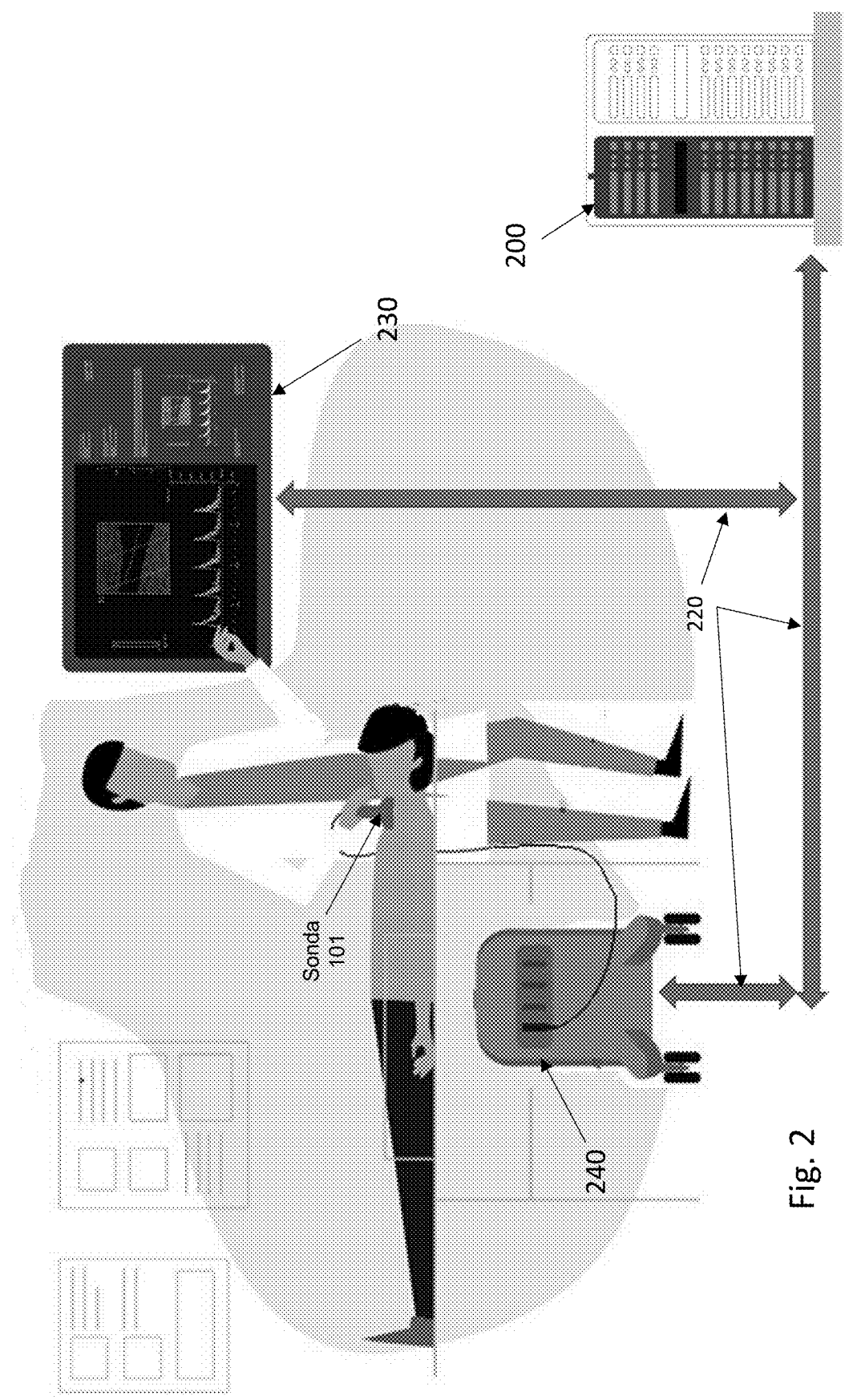
FIG. 2 shows an executive form of a possible hardware configuration of the ultrasound system according to embodiments herein.

FIG. 2 shows an executive form of a possible hardware configuration of the ultrasound system according to embodiments herein.

Figure 3:
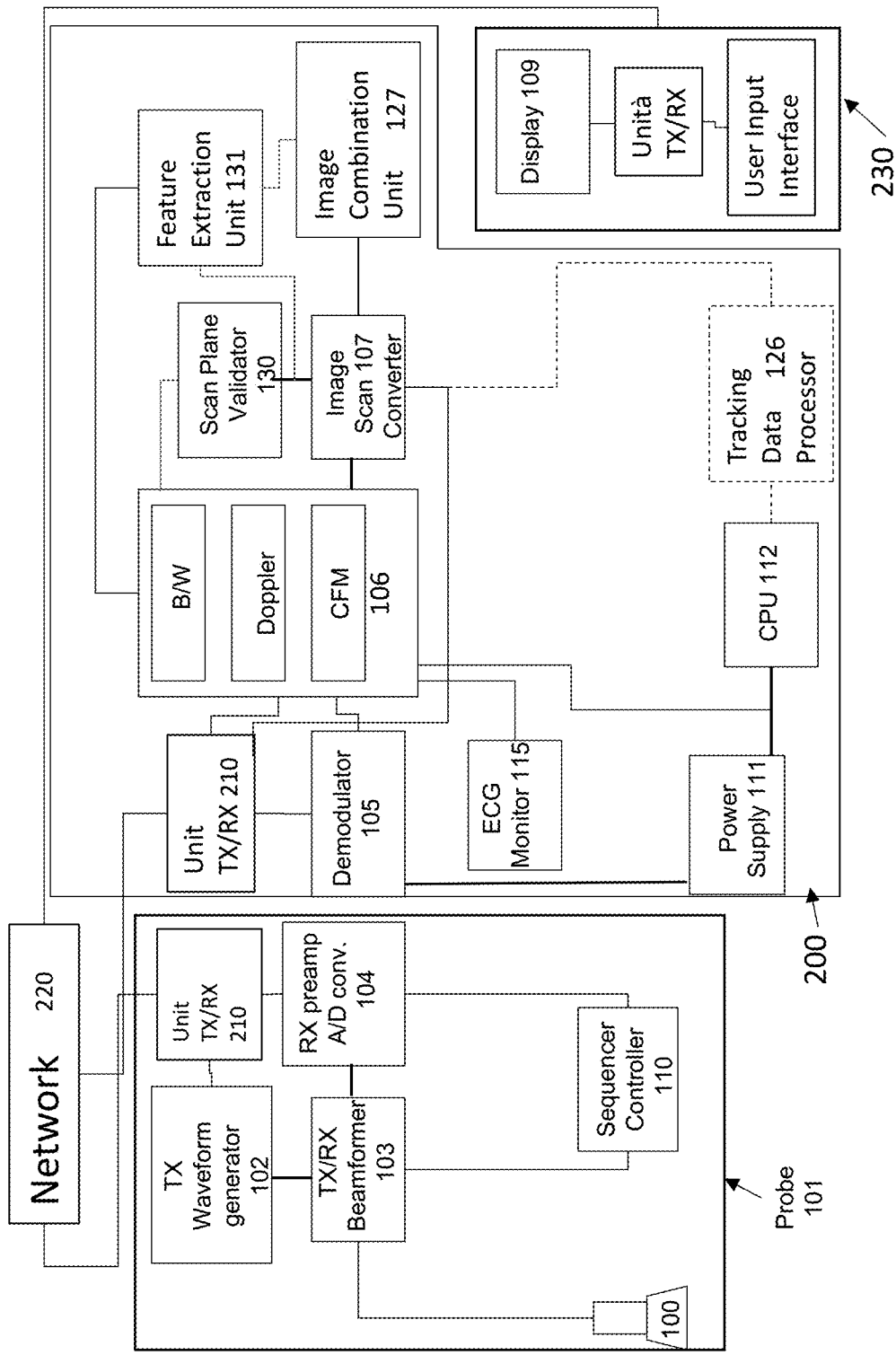
FIG. 3 shows a high-level block diagram of an ultrasound image acquisition system according to a first example embodiment.

FIG. 3 shows a high-level block diagram of an ultrasound image acquisition system according to a first example embodiment.

Figure 4:
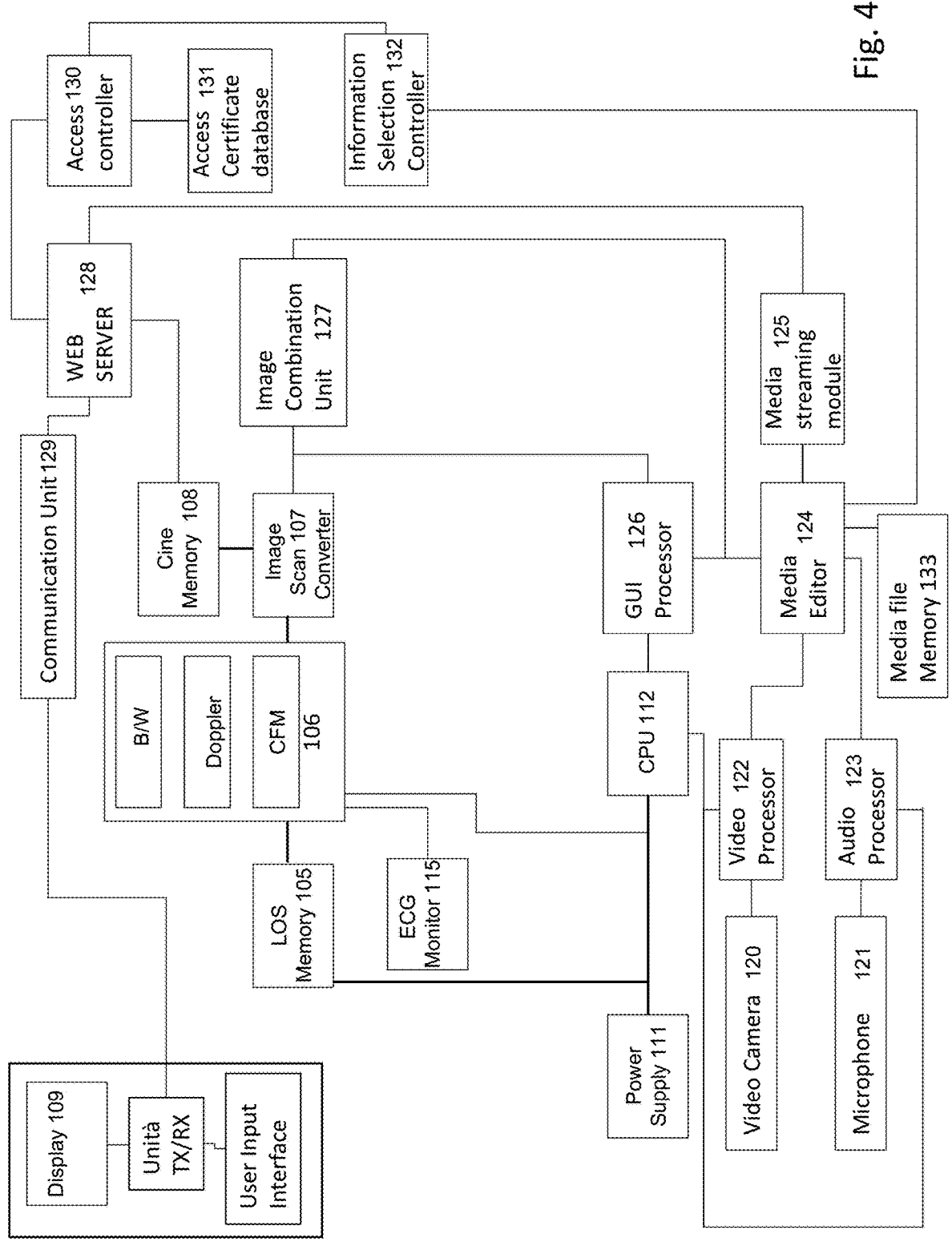
FIG. 4 shows a further embodiment of the present disclosure in which the image generation and processing unit is provided with a system for streaming the generated ultrasound images.

FIG. 4 shows a further embodiment of the present disclosure in which the image generation and processing unit is provided with a system for streaming the generated ultrasound images.

Figure 5:
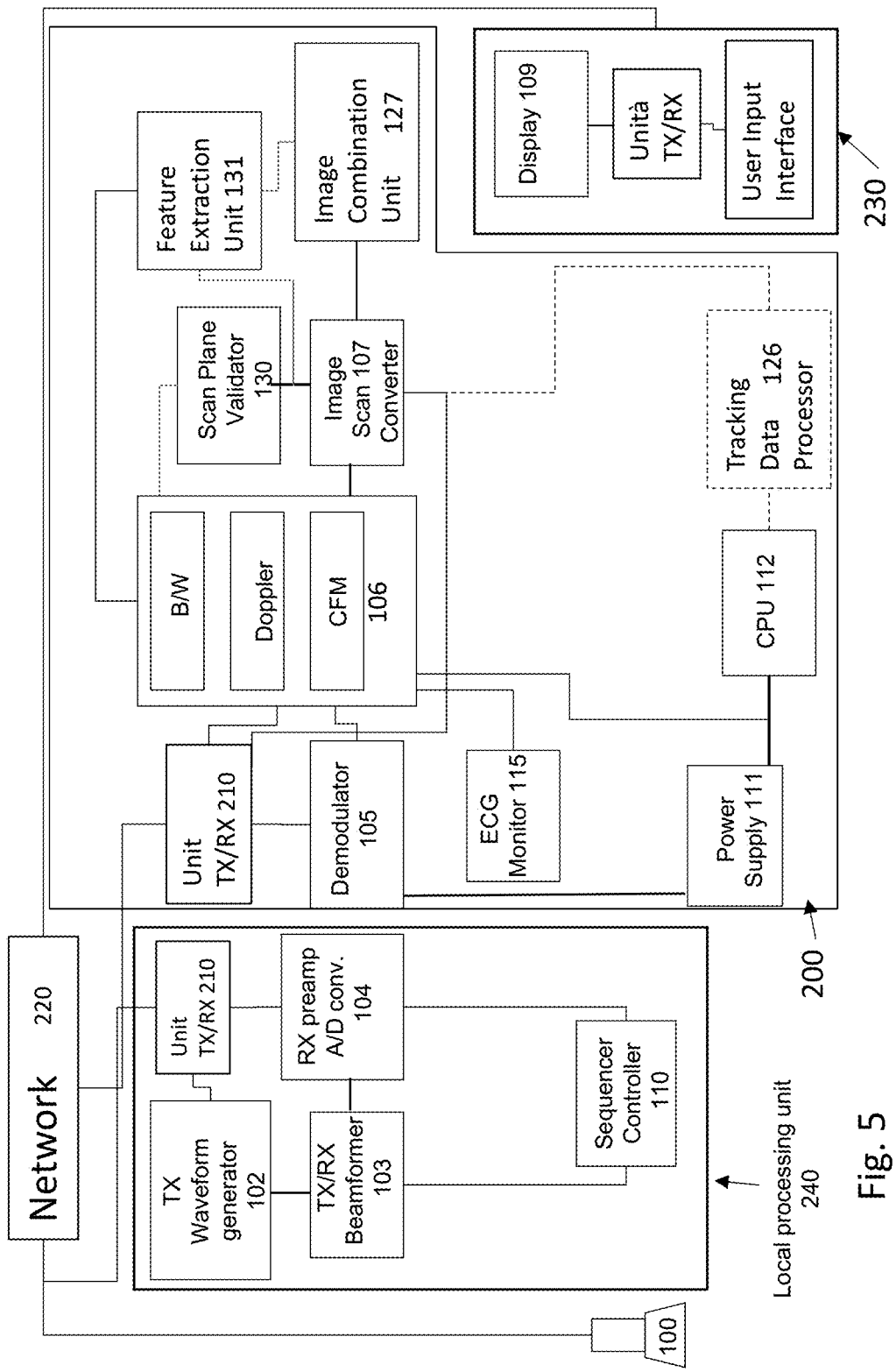
FIG. 5 shows a block diagram according to still an embodiment.

FIG. 5 shows a block diagram according to still an embodiment.

FIG. 6 shows by means of a graphic in the form of a table some different possible configurations of an ultrasound system according to embodiments herein and in particular according to FIG. 2 and corresponding variants in which the possible different subdivisions of the front-end, image forming, back-end and further processing processes of an ultrasound imaging system are shown, the process entries being to be interpreted as specific software loaded and executed by processing units provided in the probe, the local processing unit, the central processing unit and the display and user interface terminal.

Figure 7:
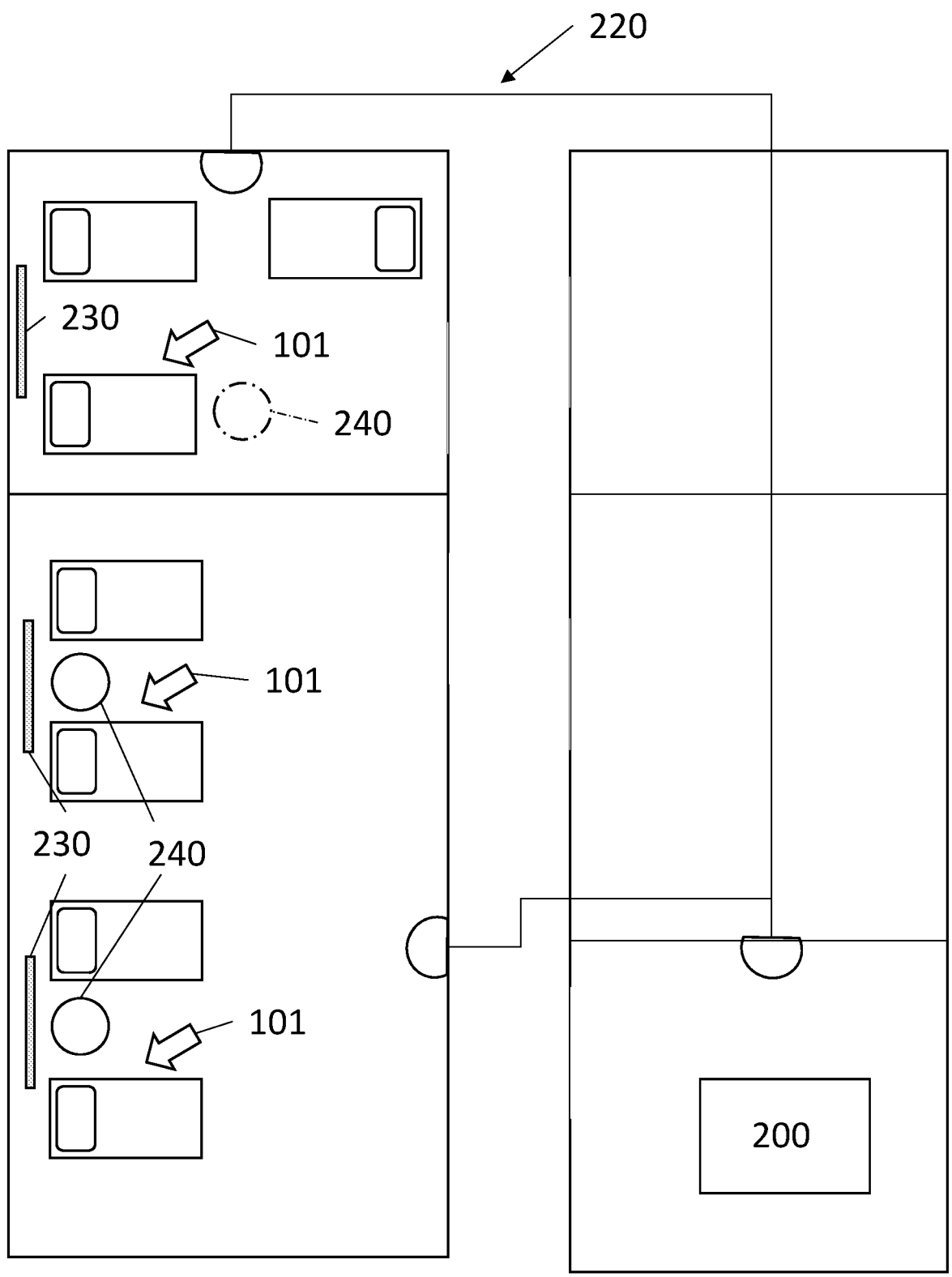
FIG. 7 schematically shows an example of an installation of the system in a hospital.

FIG. 7 schematically shows an example of an installation of the system in a hospital.

Referring to FIG. 2, the ultrasound system according to embodiments herein comprises a probe for transmitting ultrasound pulses into a body under examination and for receiving the echo signals generated by said transmission pulses. The probe typically is part of the so-called Front-End of the system. The probe denoted 101 is connected by cable or by wireless connection with a local processing unit denoted 240.

The local processing unit 240 in turn is connected via a wireless connection with a communication network 220, to a central processing unit 200. A display and user input interface terminal, such as a touchscreen 230 is also connected via wireless connection to the wireless network 220 to receive images to be displayed by the central processing unit 200 and/or to transmit user input commands to one or more of the central processing unit 200, local processing unit 240 and/or probe 101.

An embodiment variant may provide that the probe 101 is also connected to the network 220 via a wireless connection instead of a cable. In this case, the probe may connect to either the local processing unit 240 as in FIG. 2, or simultaneously also directly to the central processing unit 200 and/or the display and user interface terminal 230.

For example, for setting or diagnostic operations, the probe may connect directly to the display terminal 230 when operating with a wireless connection, while it must connect through the local processing unit or central processing unit if operating with a configuration such as illustrated.

The hardware structure of the operating units, such as the probe 101, and/or the local processing unit and/or the central processing unit and/or the display and user interface terminal have a portion of the hardware comprising a conventional type of processor, such as a microprocessor with its standard peripherals and/or a CPU with its standard peripherals or a computer such as a PC or workstation. Only a part of the hardware must necessarily be made up of ad hoc components such as transducers, screens and others.

A solution of this type of architecture is suggested by document EP1262786 whose description is incorporated by reference in this description.

Thanks to the possibility of structuring the hardware of these operating units as a generic universal and programmable processing system, it is possible to carry out the specific functions of acquisition, processing of transmission and reception signals and functions related to image formation, as well as their further processing to obtain measurements, additional information on chemical and/or physiological and/or qualitative parameters of the target under examination by means of software in which the task workflows are encoded, that is, the sequence of instructions to be executed by the processing hardware that allow this hardware and its peripherals to perform the aforementioned functions.

Therefore, migrating the hardware architecture of the ultrasound machine from an ad hoc system to a system comprising standard processing hardware running specific programs in which specific data processing functionalities are encoded for the various steps of the image acquisition, training and processing process allows the functions of the ultrasound machine to be released from the hardware structure, making the configuration of the ultrasound machine itself very flexible.

Typically, the main functions performed by an ultrasound machine consist of several processing steps including but not limited to the calculation of transmission timing, generation of digital transmission signals, D/A (digital/analog) conversion of transmission signals, A/D (analog/digital) conversion of received signals, beamforming in reception and/or transmission, subsequent operations such as data extraction by I/Q demodulation, combination of receive data related to temporally successive transmissions, envelope extraction of receive signals, compression and/or decimation of signals (steps conventionally summarized as "back end processing"), alternative processing to B-mode image generation, such as Doppler, CFM and other known state of the art, post processing on the image, scan conversion, image filtering, image enhancement and others, measurements on the image, advanced imaging modalities such as elastography, attenuation imaging and others.

Note that by migrating the functionality into software form, a system according to an example embodiment of the present disclosure can easily be adapted or modified or integrated to perform the aforementioned processes in ways that will be developed in the future, as well as to be able to perform steps new processing functions that will be developed in the future.

Thanks to the fact that it is possible to provide a conventional processing unit in each of the operating units previously described with reference to FIG. 2, an example embodiment of the present disclosure makes it possible to distribute the steps of generation of transmission signals, acquisition and processing of reception signals listed above among the said operating units.

The type of steps to be performed by each of said operating units depends in particular on the type of connection of said operating units to each other. As shown in FIG. 2, in fact, the connection, preferably of the probe to a local processing unit, can take place either through a wired connection, or through a wireless connection. This implies limitations on the data transmission speed and especially on the bandwidth available for the transmission of these data.

With regard to the available bandwidth and thus a specific distribution of the processes on the different components of the system, i.e. probe, local processing unit, central processing unit and display and user interface terminal, it seems clear that the choice of this distribution depends mainly on the number of probes, local processing units and display and interface terminals that must connect simultaneously to a common central processing unit, either directly or by means of its own dedicated local processing unit or possibly by means of a local processing unit shared by at least some of the said probes.

It is worth highlighting here the fact that it is possible to configure the system in such a way that, the processing sections associated with each operating unit or component of the system (probe, local processing unit, central processing unit, display terminal and interface) can be configured in such a way as to perform multiple processing steps, being the corresponding software loaded in the memories of the same, while it is possible to dynamically modify the processing steps performed by the various operating units, between a minimum and a maximum of said steps, depending on the bandwidth available for communication between them.

This dynamic mode of configuration according to the bandwidth can be controlled by a software that checks the available transmission speed and disables some processes in one of the operating units, enabling it at the same time in another.

The dynamic transfer of processing steps from one to another of the operating units of the ultrasound system can also take place depending, for example, on the residual power supply for one or more of the said operating units when the power supply of this or these is not from the mains, but from battery or accumulator.

Similar to software for executing transmission and/or reception signal processing steps for image acquisition, training, and processing, programs for performing specific data quantity limiting operations may be stored in one or more or all of the above operating units.

A non-exhaustive list of the main possible data quantity limiting processes is, for example:

Adaptive temporal decimation of data, depending on a predetermined bandwidth, by adjusting the sampling frequency according to the Nyquist limit (twice the maximum frequency for RF data, maximum-frequency-minimum for IQ data);

Use of a subset of receive transducers, calculated based on the maximum receive aperture actually used to combine the signals for a given transmission;

Subsampling, periodic or aperiodic, in the time domain or in the receive channel domain or both and use of compress sensing techniques for image reconstruction based on sparsity priorities in the image domain or in a transformed domain such as Fourier transform, k-space, wavelet;

Subsampling, periodic or aperiodic, in the time domain or in the receiving channel domain or both, and use of machine learning techniques for reconstruction of missing data;

Subsampling by reducing the number of data by multiplying the received signals by a matrix with fewer rows than the number of columns;

use of advanced beamforming techniques that allow to obtain images of equal or similar quality compared to standard line-by-line beamforming, reducing the number of transmissions and therefore the amount of data required to form a frame, such as those in the following list: multiline receive beamforming, synthetic transmit beamforming (STB), retrospective transmit beamforming (RTB), synthetic aperture imaging, plane wave or diverging wave beamforming;

combination of synthetic aperture-based beamforming or plane wave or diverging wave beamforming, with a reduction in the number of transmissions and with a machine learning algorithm that maps low-quality images obtained with a limited number of insonifications, to images that reproduce the characteristics of high-quality images that would have been obtained with a higher number of insonifications;

two-stage beamforming or microbeamforming in which a part of the beamforming is performed on the probe on distinct groups of transducers, thus reducing the number of communication channels between probe and apparatus and consequently the data transfer rate, and in which the further part of the beamforming is performed by a local and/or central processing unit, being instructions for the execution of said processes encoded in a corresponding program that is loaded and executed by the processing unit of said probe(s) and/or said local unit(s) and/or said central unit(s) and wherein the execution of said program configures said processing unit(s) and associated peripheral(s) to perform the functions of said one or more data quantity reduction processes to be transmitted between said probe(s) and/or said local processing unit(s) and/or said central processing unit(s).

These processes of reducing the amount of data have been described in greater detail in the foregoing description with reference also to published documents which are to be considered incorporated into the present description.

FIG. 3 shows a first concrete executive example of splitting an ultrasound system and processing functions onto only three of the four different operating units of the distributed ultrasound system consisting of the probe 101, a central processing unit 200 and a display and interface terminal 230. A communication network 220 enables data exchange between said operating units. The connection may be wired or wireless.

The system has substantially the same functional blocks present in the executive form according to the state of the art. Therefore, the same reference numbers are used in the figure as in FIG. 1.

As is apparent, in FIG. 3, the probe 101 includes in addition to the set of electroacoustic transducers 100, the beamformer 103 for focusing the beams of ultrasonic pulses in transmission and/or reception according to one or more of the various modes already described above and which are intended to reduce the amount of data to be transmitted between the probe and a central processing unit indicated by 200. A waveform generator 102 is intended to generate electrical pulses to drive individual electroacoustic transducers 100 to the emission of an ultrasonic pulse having a waveform corresponding to that of the driving signal. A sequence controller 110 for emitting and/or receiving ultrasonic pulses controls the process of transmitting and receiving and provides for switching at least part of the electroacoustic transducers so that they are suitable for transmitting and/or receiving ultrasonic signals. The electrical signals generated by the transducers as a result of receiving ultrasonic echo pulses, i.e., reflections from the body under examination into which the ultrasonic transmission pulses were transmitted are preamplified and possibly sampled by means of an analog-to-digital converter 104.

The received signals are then transmitted by means of a receiving/transmitting unit 210 which connects to a communication network 220 to a central processing unit 200 which consists of an image generation and processing server, which server 200 is physically separated from the probe, i.e., located at a site remote from the site where the examination is performed by scanning with the probe 101. The central processing unit has operating modules for performing processing of the receive signals provided by the probe via the network 220 to which it is connected via a transmit/receive unit also indicated by 210. The central processing unit 200 is configured, in this example to perform processing steps related to image formation, back-end processing, and further image processing steps according to the definitions more fully set forth above.

In relation to the detailed description of the functional blocks, reference is made to the description in FIG. 1.

In addition, the central unit 200 is in communication with a display and/or a user interface terminal 230 that is also provided with a TX/RX communication unit connected to the communication network 220. This terminal may comprise a screen in combination with command or data entry means such as a keyboard or the like, or it may be of the touch screen type in combination with a graphical user interface that is represented on the screen 109 itself.

Already from the foregoing description, an advantage of the example embodiments of the present disclosure becomes clear. In fact, the central processing unit 200, although shown in the form of a combination of operating modules, can easily be constituted by a conventional processing system executing programs in which instructions are encoded to command said processor and any peripherals thereof to perform the functions of the individual operating organs illustrated.

Furthermore, ensuring sufficient bandwidth, the same central processing unit may serve for image generation and/or processing and displaying the same from image data received from two or more different ultrasound probes that are used simultaneously, for example on different patients and whose images are displayed on one of a plurality of terminals univocally associated, temporarily with a predetermined probe and that is for the duration of the examination.

In this condition, the executive form is advantageous in which each probe 100 and each display and/or user interface terminal 230 is univocally associated with an identification code, and that the central image generation and/or image processing unit 200 also executes a program for managing the identification codes of the probes and/or terminals 230 that univocally associates according to predetermined criteria a probe 100 with a terminal 230.

A criterion for association between a probe and a terminal of a plurality of terminals distributed in an environment may comprise the relative distance between the probe and the terminal, and alternatively or in combination whether a spatial relationship exists between the probe and the terminal such that there is no impediment to direct viewing of the terminal by a user at the location of the probe.

A possibly advantageous form of implementation envisages that the probes and terminals are provided with position identification units within a virtual map of the places of use and installation, and that on the basis of said position relative to the map and relative to each other the central unit automatically associates a terminal with a probe when the distance between them is the minimum detected and/or the relative position allows a direct and unobstructed view of the terminal from the position of the probe, for example when the terminal and the probe are not separated by walls or other divisions indicated in the virtual map.

According to yet another feature that can be provided in combination or separately, the probe and/or terminal are provided with the necessary hardware and software to perform the association operations according to one or more of the criteria described above. In this case, an advantageous variant comprises providing the hardware and software for managing the association between the probe and the display and/or user interface terminal, in said terminal.

The communication network may be a traditional communication network according to the TCP/IP protocol or other similar network protocols, and communication may be via a wired connection.

For example, in a ward or department, each bed can be associated with a socket for connecting a network cable to which the probe can be connected, while the display terminals can be provided supported on the wall by special arms that can be oriented, for example, every two beds.

According to a preferred variant, the communication between at least the probe and the network 220 takes place via a wifi connection.

In this case it is advantageous to provide a configuration of the probe and the processes of image data acquisition by ultrasound such that the amount of data to be transferred from the probe to the central processing unit is limited, thus allowing the simultaneous use of multiple probes while maintaining the speed of communication sufficiently high to allow you to perform image acquisitions at the level of systems according to the state of the art.

This consideration can also be extended to display and/or user interface terminals, as wireless connection of these terminals as well would allow for savings relative to installation costs and greater freedom in positioning and/or moving said terminals.

According to an executive form, instead of transmitting traditional digital video signals to the displays of the visualization terminals, it is possible to use a transformation of the generated ultrasound images into streaming video signals that are then transmitted to the monitors by means of protocols derived from streaming transmission.

This form of implementation is illustrated in the high-level block diagram in FIG. 4. Again, blocks common in function to the preceding examples have the same reference numerals and will not be described in detail, but reference is made to the description relating to the preceding FIGS. 1 and 2 which also finds application to this form of implementation.

One or more processors 106 perform various processing operations as described herein. The CPU 112 may perform control operations of various units such as the processors 106, the GUI image processor 162, the video processor 122, and the audio processor 123.

Among other things, the processor 106 and/or CPU 112 analyze image pixels to determine the differences between each successive image from a preceding image of a temporal sequence of images and to control the video processors and/or multimedia editor or streaming module 125 to discard from the data stream to be transmitted to the display terminals images that are identical or nearly identical to the preceding image while maintaining the preceding image on the screen and avoiding transmitting said subsequent image unchanged from the preceding image.

The processor 106 and/or the CPU 112 also perform conventional ultrasonic operations. For example, the processor 106 performs a black and white module to generate B-mode images. The processor 106 and/or CPU 112 execute a Doppler module to generate Doppler images. The processor executes a color flow module (CFM) to generate color flow images. The processor 106 and/or CPU 112 may implement additional ultrasound imaging and measurement operations. Optionally, the processor 106 and/or CPU 112 may filter displacements to eliminate motion-related artifacts.

An image scan converter 107 performs scan conversion on image pixels to convert the image pixel format from the coordinate system of the ultrasound acquisition signal path (e.g., the beamformer, etc.) and the display coordinate system. For example, the scan converter 107 may convert image pixels from polar coordinates to Cartesian coordinates for image frames.

A local display 109, i.e., at the image generation unit 200 displays various ultrasound information, such as image frames and measured information according to embodiments herein. The display 109 displays the ultrasound image with the region of interest shown. Optionally, the system of FIG. 3 may include an ECG monitor 115 that couples an ECG sensor to the patient and records an ECG signal indicative of the patient's heart rate. The processor 106 and/or sequence controller 110 synchronize the image acquisition steps with the ECG signal.

A control module 112 is configured to perform various tasks such as user/interface implementation and general system configuration/control. In the case of fully software implementation of the ultrasound signal path, the processing node normally also houses the functions of the control CPU.

The acquired images as well as GUI images and text data are combined in the image combination unit 127 and the combined images are displayed on the local display 109 of the central image generation and processing unit.

Said captured images and GUI images and text data are also processed by a multimedia editor 124. The multimedia editor 124 is configured to combine the captured images, GUI images, and text data as well as other data such as acoustic data and additional video images to generate a multimedia video clip encoded as a media file according to one or more of the currently available encoding protocols for video and acoustic files.

Acoustic data can be generated by the ultrasound system as the audio files representing blood flows in various flow imaging modalities such as Doppler, power Doppler, etc. According to a variation shown in the figure, acoustic data can also be generated by a microphone 121 that captures noise or speech delivered by one or more operators using the system. The microphone signals are fed to an audio processor 123 that is configured to encode the acoustic signals into audio files. The audio files are sent to the media editor to be associated with one or more of the further images in a manner synchronized with the content of at least one of said images.

The further image data may be captured by a camera 120 imaging, for example, personnel serving the central processing unit, the ultrasound system or part thereof, a patient or an anatomical district of a patient, and at least one of the operators of the ultrasound system. The image data captured by the camera is processed by a video processor 122 and also sent to the multimedia editor to be combined in a multimedia embodiment with audio files and/or with one or more of the captured images and/or with GUI images and/or with images reproducing textual or alphanumeric encoded data.

The multimedia editor 124 may be configured by user settings and/or factory presets to combine image information and audio information according to various schemes by generating a common media file or the captured images and/or GUI images and/or images reproducing textual or alphanumeric data, the one or more audio files are made available as separate media files that may be downloaded and displayed in parallel in different areas of a client display and in a synchronized manner for at least some of said images and/or audio files.

The media files generated by the media editor are sent to a multimedia streaming module 125 that can be accessed via a web server 128 by a client that connects to a communication unit or port 129 of the ultrasound system.

The client is configured to run a browser that allows access to the media content via the web server 129.

For example, the client is included in the display and/or user interface terminal and connects to the web server 129 to stream images related to image data provided to the central image generation and/or processing unit 200 from the probe 101.

According to a further feature, access to the streaming media is governed by an access controller 130 that receives certificates or credentials of access rights, such as user ID and password and/or in this case the ID of the display and/or user interface terminal associated with a probe. The access controller 130 compares the certificates sent by the client at the request of the web server 128, with the certificates stored in an access certificate database 131, and if the certificates sent to the access controller 130 match the certificates stored at said database 131 access to is permitted to the multimedia streaming module 125 for downloading media content.

According to a further feature, the access certificates may also contain parameters indicating which parts of the encoded information such as scanned images, GUI images, textual and alphanumeric data, and audio files may be left free for access by the corresponding client and which parts of said information are not available to said client. This parameter is identified and processed by an information selection controller 132 that is configured to identify what portion of the information data is to be made available to the client that has submitted access credentials and what portion is not to be made available. The information selection controller 132 works with the multimedia editor 124 to block the transfer of the identified unavailable data and to allow access to the available information.

The multimedia editor 124 may also be configured to make some of the visual and/or auditory information unavailable by covering the display areas where this information is printed on the display screen by a banner and muting the audio files or portions thereof.

According to one embodiment, the media files generated by the multimedia editor 124 may be stored in a media file memory 133 and access to said file via the multimedia streaming module 125 may be performed in real time or at a later time relative to the time of generation of the visual and/or acoustic information by an off-line streaming process.

The various units and processors 122, 123, 124, 125, 126, 128, 130, 132 may consist in whole or in part thereof of dedicated hardware.

In an alternative embodiment, said units and processors may consist of at least a portion thereof of a dedicated general purpose processing unit executing a software program in which instructions are encoded to configure the general-purpose processing unit in performing the functions of the specific processor and/or unit 122, 123, 124, 125, 126, 128, 130, 132, e.g., from the same central generating and/or image processing unit.

In a further variation, at least part of said units and processors may comprise software that is executed by CPU 112 configuring said CPU and its peripherals to perform the functions of said at least part of units and processors 122, 123, 124, 125, 126, 128, 130, 132.

The web server software operates according to the http protocol. Many commercially available web server software may be used from among the various web server software currently available, such as Apache pf Apache Software Foundation, nginx by NGINX, Inc, IIS by Microsoft Corporation, Lite Speed Web Server by LiteSpeed Technologies, GWS by Google LLC.

With reference to the client many possible web browsers can be run, the most popular of which are Google Chrome from Google LLC, Mozilla Firefox from Mozilla Corporation, Internet Explorer and Microsoft Edge from Microsoft Corporation.

Examples of media editors are Windows media editor from Microsoft Corporation, MPEG editor from Multimedia Inc. and other various software houses.

The multimedia streaming module can be configured according to the Microsoft Multimedia Streaming architecture described in https://msdn.microsoft.com/en-us/library/windows/desktop/dd373418(v.vs.85). aspx and pages linked to it. The description of this architecture is incorporated here by reference.

As will become clearer from the following description, any type of client hardware can be used to connect to the web server and access the multimedia files in the ultrasound system by applying live streaming technology. During the generation of the visual and/or auditory and/or textual information, the same information or only a selected portion thereof may be downloaded as a multimedia file, in real time to an unrestricted number of clients and played by the clients' visual and audio playback units, such as a display and a speaker.

Multimedia files can be stored in the client to have the ability to view them one or more times in an off-line client process from the server.

The hierarchy of access rights credentials allows selecting the information made available to specific clients or users.

Since it is possible to combine different types of visual information and audio information, it is possible not only to share the images captured by the ultrasound system and/or combined with the GUI image and any textual information associated with the captured images, but it is also possible to record visual and audio information related to the tutorial explanation of the system, the way to use and set it up, and the way to perform examinations such as manipulating the probe in relation to the specific anatomical district to be examined.

FIG. 5 is a block diagram illustrating a different subdivision of the functional blocks of the diagram in FIG. 1 or 2 than the subdivision in FIG. 2.

With reference to FIG. 5, unlike the executive form of FIG. 3, the probe comprises only the electroacoustic transducers and has no processing function. The probe is connected analogously to the example of FIG. 2 to a local processing unit 240. The connection may be via wireless or wired connection, either directly or through a communication network indicated by 220.

The local processing unit includes function blocks 102, 103, 104 and 110 for performing transmit and receive beamforming operations according to one or more of the beamforming modes more fully described above.

A communication unit 210 connects the local processing unit to the communication network 210 to which a central processing unit 200 is connected.

This central processing unit 200 communicates with the local processing unit 240 by means of the network 220 or directly via a wired or preferably wireless connection.

The central processing unit comprises various blocks for performing demodulation 105, image data processing for the various imaging modes 106, scan converter 107 and other image post-processing processing. The formed image is then transmitted to one of the terminal display and/or interface devices 230 which in this example include a display 109, the user interface unit and a network communication unit 220 and/or also separately and directly with the probe and/or local processing unit 240 and/or central processing unit 200.

From the various forms of implementation illustrated, it is evident how example an embodiment of the present disclosure allows the operating units Probe, local processing unit, central processing unit and display and user interface terminal to be configured in such a way as to confer on each of these units different data processing functionalities in order to guarantee, depending on the contingent conditions, the best performances in terms of efficiency and image quality.

FIG. 5 shows in tabular form various examples of the distribution of processing steps for the acquisition and generation of ultrasound images on the various operating units 101, 240, 200 and 230 defined above.

Although the table shows the functions, i.e. the processing steps, this representation is only iconic and is intended to simplify the structure of the individual operating units in relation to the processing steps so that they can be easily compared. This structure is essentially identical for each of the operating units of the system, being the units that execute the processing steps constituted by a computer with a conventional hardware, which runs specific software in which are coded instructions to perform each of the functions each time assigned to one of these operating units.

Thus, it appears that each of the operating units consisting of the probe and optionally of a local processing unit, a central processing unit and a display and user interface terminal substantially differs in principle with respect to the processing steps attributed to it by the fact of having loaded the corresponding software and executing it.

Each box in the table is thus to be regarded as a combination of processing hardware executing a program in which instructions are encoded to make the hardware capable of performing the indicated function.

With reference to FIG. 22, this shows very schematically an example of a system in a hospital or other healthcare facility. In the rooms intended to house the patients there is a WiFi access point to a network 220 of communication with a centralized image generation and processing server indicated with 200 and which assumes all the typical functions of an ultrasound scanner in relation to the generation of images from image data acquired by a probe and any processing of the same.

The server is capable of performing functions on image data acquired by three different probes on three different patients. The probes 101 transmit via wifi communication and with their unique identification code the image data to the central unit 200. This in turn, after having generated the image, transmits the generated images and/or the processing results to the corresponding monitors 230 via the network 220. The action takes place in real time or with a time shift such that it can be considered in real time and allow the user to have the same sensations and experiences of image acquisition and visualization as with a traditional ultrasound scanner. Thanks to probe IDs univocally associated with a corresponding monitor 230 the images of each probe 101 are displayed in the monitor closest to them.

Local processing units are shown with 240. According to one embodiment, these local units may each be provided for only one patient station and thus for only one probe per examination. In contrast, an executive variation illustrated in the figure provides that the local unit 240 may be associated with two or more patient stations and thus with two or more probes performing two different examinations simultaneously. A local unit with a discontinuous line is shown at the top of FIG. 22 to show the executive variant in which one or more probes communicate directly with a central processing unit 200 being this central unit configured to perform all processing steps attributable to the local unit that is omitted, in addition to those attributed to the central unit itself.

The invention claimed is:

1. A multi-user system for acquiring, generating, and processing ultrasound images, said system comprising:
   a plurality of ultrasound probes configured to scan patients at predetermined examination sites and provided with a communication unit for transmitting corresponding data to a processing unit also provided with another communication unit;
   a plurality of display and/or user interface terminals provided in a vicinity of the examination sites and provided with yet another communication unit for transmitting to, and receiving data from, said processing unit and/or one or more of said probes;
   a communication network connecting together the respective said communication units of said probes, said display and/or user interface terminals and said processing unit;
   said probes and said display and/or user interface terminals each being identified by a corresponding ID;
   said processing unit being configured to receive scanning signals detected by each or at least one of said probes and process said signals to generate ultrasound images, optionally process said ultrasound images and transmit said images and/or the outputs of said optional processing to one or more of said plurality of display and user interface terminals univocally associated with the probe that transmitted the data from which the images and/or processing thereof was generated;

in said processing unit are loaded programs in which are coded instructions to receive data from each of said probes and to generate the corresponding images and/or to perform the corresponding processing, and/or to associate each probe to a pre-established patient and/or to a pre-established service person and/or to a pre-established display terminal and to receive from the user interface terminal possible commands and/or setting data, said instructions being executed by said processing unit upon execution of said program, wherein the processing unit has a distributed structure comprising at least two, preferably three, optionally at least four or more processing units each of which are integrated respectively in the probe and/or in an optional local processing unit associated with one or more patient workstations and dedicated to a single probe or a partial number of probes and possibly positioned in an immediate vicinity of said one or more patient workstation(s) and/or in a remote central processing unit which is associated with all and/or at least some of said probes and/or said local processing units, and/or with one or more of said plurality of display and user interface terminals, said processing units communicating with each other;

the processing steps of the reception signals of said probe or probes being divided in said processing units in such a way that one or more of said processing units execute programs in which are encoded instructions for making said operating units capable of executing only a part of the processing steps;

wherein the system further comprises applying alternately with each other and/or, when possible, also in any combination thereof one or more data reduction processes selected from the following list:

Adaptive temporal decimation of the data, as a function of a predetermined bandwidth, by adjusting the sampling frequency according to the Nyquist limit of twice the maximum frequency for RF data or maximum-frequency-minimum frequency for IQ data;

Use of a subset of receive transducers, calculated from the maximum receive aperture actually used to combine signals for a given transmission;

Sub-sampling, periodic or aperiodic, in the time domain or in the receive channel domain or both and use of compress sensing techniques for image reconstruction based on sparsity priorities in the image domain or in a transformed domain such as Fourier transform, k-space, wavelet;

Sub-sampling, periodic or aperiodic, in the time domain or the receiving channel domain or both, and use of machine learning techniques to reconstruct missing data;

Sub-sampling by reducing the number of data by multiplying the received signals by a matrix with fewer rows than the number of columns;

Use of advanced beamforming techniques that allow to obtain images of equal or similar quality compared to standard line-by-line beamforming, reducing the number of transmissions and thus the amount of data required to form a frame, such as those in the following list: multiline receive beamforming, synthetic transmit beamforming (STB), retrospective transmit beamforming RTB), synthetic aperture imaging, plane wave or diverging wave beamforming;

combination of beamforming based on synthetic aperture or plane wave or diverging wave beamforming, with a reduction in the number of transmissions and with a machine learning algorithm that maps low quality images obtained with a limited number of insonifications, onto images that reproduce the characteristics of high quality images that would have been obtained with a higher number of insonifications;

Two-stage beamforming or microbeamforming in which part of the beamforming is performed on the probe on distinct groups of transducers, thus reducing the number of communication channels between probe and apparatus and consequently the data transfer rate, and in which the further part of the beamforming is performed by a local and/or central processing unit;

the instructions for the execution of said processes being encoded in a corresponding program which is loaded and which is executed by the processing unit of said probe/s and/or said local unit(s) and/or said central unit/sand wherein the execution of said program configures said processing unit/s and associated peripherals to perform the functions of said one or more processes for reducing the amount of data to be transmitted between said probe(s) and/or said local processing unit/s and/or said central processing unit/s.

2. System according to claim 1 wherein there are provided one or more processing programs in which are encoded instructions for making said one or more processing units capable of executing each all or only part of the processing steps selected from the following list:

the calculation of the transmission timing, the generation of the digital transmission signals, the D/A (digital/analog) conversion of the transmission signals, the A/D (analog/digital) conversion of the received signals, the beamforming in reception, the subsequent operations generically defined in the technical field as "back end processing" such as the extraction of I/Q data from the beamformed reception signals, the combination of reception data related to temporally successive transmissions, envelope extraction of receive signals, signal compression and decimation, alternative processing to B-mode image generation, Doppler, CFM and other modalities, post processing activities on the image, scan conversion, image filtering, image enhancement and other optimization processing on the image, measurements on the image, as well as advanced imaging modalities such as elastography, attenuation imaging and combinations of one or more of the above listed steps.

3. A system according to claim 1, wherein the probe(s) and/or the local processing unit(s) and/or the central processing unit(s) and/or the display and/or user interface terminal(s) may communicate alternatively or in combination by a selection of the communication mode via a wired connection and/or a wireless connection.

4. System according to claim 1, wherein a local unit id associated with a group of patient stations, e.g., two or more patient stations, a probe being provided for each station and/or for two or more stations of said group and, alternatively or in combination, a central processing unit operating in combination of one or more groups of patient stations comprising probes and/or local processing units.

5. A system according to claim 1, wherein said system is configured according to one of the configurations selected from the following list:
a)
- at least one of the probes is connected to local processing units via analogue cable;
- the D/A conversion in transmission (TX), A/D conversion in reception (RX) are performed on a local processing unit, and the beamforming in transmission and/or reception (TX/RX) and further processing are performed on a central processing unit;

b)
- at least one of the probes is connected to local processing units via analogue cable;
- D/A conversion in transmission (TX), A/D conversion in reception (RX) and beamforming in transmission and/or reception (TX/RX) are performed on a local unit and further processing is performed on a central processing unit;

c)
- at least one probe is wired or wirelessly connected to a local processing unit with a digital connection;
- D/A conversion in transmission (TX), A/D conversion in reception (RX) are performed on the probe and beamforming in transmission and/or reception (TX/RX) and back-end processing are performed on a local processing unit and further processing is performed on a central processing unit;

d)
- at least one probe is wired or wirelessly connected to a local processing unit with a digital connection;
- the D/A conversion in transmission (TX), A/D conversion in reception (RX) and beamforming in transmission and/or reception (TX/RX) are performed on the probe and the back-end processing is performed on a local processing unit and the further processing is performed on a central processing unit;

e)
- at least one probe is wired or wirelessly connected to a local processing unit with a digital connection;
- D/A conversion in transmission (TX), A/D conversion in reception (RX) are performed on the probe, beamforming in transmission and/or in reception (TX/RX) is performed partly on the probe and partly on a local processing unit and back-end processing is performed on a local processing unit and further processing is performed on a central processing unit;

f)
- at least one probe is connected to a local processing unit by cable with an analogue or a digital connection;
- transmission signal generation and beamforming in transmission are performed on the probe, A/D conversion in reception (RX) and beamforming in reception are performed on a local unit and back-end processing and further image processing are performed on a local or central unit;

g)
- at least one probe is connected to a local processing unit by cable with an analogue or digital connection;
- transmission signal generation, beamforming transmission and beamforming in reception, partial analogue are performed on the probe, A/D conversion in reception (RX) is performed on a local unit, while further beamforming steps, back-end processing and further image processing are performed on local or central unit and some further processing steps are performed only on a central unit.

6. System according to claim 1, wherein the local processing unit/s are omitted and the functions performed by the local processing unit/s according to any one of the above described forms and variants of performance are performed by the probe and/or a central processing unit or said functions are divided between the probe and said one central processing unit.

7. System according to claim 1, wherein the probe may comprise a DAC/ADC conversion unit and a beamforming unit in transmission and/or in reception, or alternatively a DAC/ADC conversion unit, a beamforming unit in transmission and/or reception and back-end processing unit, or according to yet another alternative, a beamforming unit in transmission and/or reception, one or more back-end processing units and a scan converter, as well as optionally units for performing further image processing, in which case only the already formed ultrasound images are transmitted to a central processing unit.

8. System according to claim 1, wherein the system further comprises applying alternately with each other and/or, when possible, also in any combination thereof one or more data reduction processes selected from the list in claim 1, and
- Two-stage beamforming or microbeamforming in which part of the beamforming is performed on the probe on distinct groups of transducers, thus reducing the number of communication channels between probe and apparatus and consequently the data transfer rate, and in which the further part of the beamforming is performed by a local and/or central processing unit.

9. System according to claim 1, wherein said central processing unit comprises a module for encoding images generated in the form of video files and a streaming module for streaming the ultrasound images to the display terminal.

10. System according to claim 9, further comprising a comparator unit that compares each successive video and/or acoustic frame with the preceding one and discards from the media file to be generated the video frames that are identical with the preceding ones while retaining in the video file only the video frames that are different from the preceding ones.

11. A system according to claim 1, wherein there is provided a controller that measures the frame rate of the frames displayed on the display of the client, said controller driving a unit for discarding video frames from said media data stream, said unit being configured to discard video frames from said media data stream and optionally associated acoustic data when the frame rate of the displayed frames falls below a certain threshold, there being also provided an input interface for setting said threshold.

12. A system according to claim 1, further comprising a meter unit for measuring the available bandwidth for connection between probes, local processing units, central processing units and display and user interface terminals, which meter unit modifies the distribution of processing steps on the probes and/or on the local processing units and/or on the central processing unit and/or on the display and user interface terminals by enabling and disabling the execution of software encoding instructions to execute said processing steps on the probes and/or on the local processing units and/or on the central processing unit and/or on the display and user interface terminals, respectively, on the local processing units, on the central processing units and/or on the display and user interface terminals according to the bandwidth for connecting said probes, local processing units, central processing units and display and user interface terminals to each other.

* * * * *